(12) United States Patent
Trower

(10) Patent No.: US 9,907,795 B2
(45) Date of Patent: *Mar. 6, 2018

(54) METHOD OF TREATMENT OF CHRONIC COUGH ADMINISTERING ORVEPITANT IN COMBINATION WITH OTHER THERAPEUTIC AGENTS

(71) Applicant: NeRRe Therapeutics Limited, Herts (GB)

(72) Inventor: Mike Trower, Herts (GB)

(73) Assignee: NeRRe Therapeutics Limited, Herts (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/666,568

(22) Filed: Aug. 2, 2017

(65) Prior Publication Data

US 2017/0326141 A1 Nov. 16, 2017

Related U.S. Application Data

(63) Continuation-in-part of application No. 15/390,770, filed on Dec. 27, 2016, now Pat. No. 9,750,739.

(60) Provisional application No. 62/276,237, filed on Jan. 8, 2016, provisional application No. 62/408,921, filed on Oct. 17, 2016.

(51) Int. Cl.
| | |
|---|---|
| *A61K 31/4985* | (2006.01) |
| *A61K 31/4418* | (2006.01) |
| *A61K 31/496* | (2006.01) |
| *A61K 31/5377* | (2006.01) |

(52) U.S. Cl.
CPC ...... *A61K 31/4985* (2013.01); *A61K 31/4418* (2013.01); *A61K 31/496* (2013.01); *A61K 31/5377* (2013.01)

(58) Field of Classification Search
None
See application file for complete search history.

(56) References Cited

U.S. PATENT DOCUMENTS

2015/0057299 A1* 2/2015 Ford ............... C07D 239/48
514/272

FOREIGN PATENT DOCUMENTS

WO WO 2014117274 A1 * 8/2014 ........... C07D 471/04

OTHER PUBLICATIONS

Ford, A.P., Purinergic Signalling, 8:S3 (2012).*
Hörig et al., J. Translational Med. 2:44 (2004).*
NCT01432730 (Jan. 6, 2014).*
NCT01979952 (Jan. 8, 2014).*
Okazaki, et al., Pulmonary Pharmacology & Therapeutics, 26:603 (2013).*
Bae Y.G., et al., "The role of nitrosative stress in the pathogenesis of unexplained chronic cough with couggh hypersensitivity", Am J Rhinol Allergy. Jan.-Feb. 2012;26(1):e10-4.
Belvis MG, et al., "Cough. 7: Current and future drugs for the treatment of chronic cough" Thorax. May 2004;59(5):438-40.
Bolser D.C., et al., "Central antitussive activity of the NK1 and NK2 tachykinin receptor antagonists, CP-99,994 and SR 48968, in the guinea-pig and cat", Br J Pharmacol. May 1997;121(2):165-70.
Bolser D.C., et al., "Influence of central antitussive drugs on the cough motor pattern", J Appl Physiol (1985). Mar. 1999;86(3):1017-24.
Canning B.J., "Central Regulation of the Cough Reflex: Therapeutic Implications", Pulm Pharmacol Ther. Apr. 2009;22(2):75-81. Epub Jan. 20, 2009.
Canning B.J., et al., "Anatomy and neurophysiology of cough: Chest Guideline and Expert Panel report", Chest. Dec. 2014;146(6):1633-48.
Chapman , et al., "Antitussive activity of the tachykinin NK1 receptor antagonist, CP-99994, in dogs", Eur J Pharmacol. Feb. 6, 2004;485(1-3):329-32.
Chapman R.W., et al., "Antitussive activity of the tachykinin NK1 receptor antagonist, CP-99994 in dogs", European Journal of Pharmacology 485 (2004) 329-332.
Chen C.Y, et al., "Central mechanisms I: plasticity of central pathways", Handb Exp Pharmacol. 2009;(187):187-201.
Chung K.F., "Approach to chronic cough: the neuropathic basis for cough hypersensitivity syndrome", J Thorac Dis. Oct. 2014;6(Suppl 7):S699-707.
Chung K.F., "NMDA and GABA receptors as potential targets in cough hypersensitivity syndrome", Current Opinion in Pharmacology, 2015, 22:29-36.
Chung K.F., et al., "Eight International London Cough Symposium 2014: Cough hypersensitivity syndrome as the basis of chronic cough", Pulmonary Pharmacology & Therapeutics 35 (2015) 76-80.
Chung K.F., et al., "Prevalence, pathogenesis, and causes of chronic cough", Lancet. Apr. 19, 2008;371(9621):1364-74.
clinical Trials Register 2014-00394, date available to the public Jan. 12, 2015.
El-Hashim AZ et al, "Effect of a novel NK1 receptor selective antagonist (NKP608) on citric acid induced cough and airway obstruction", Pulm Pharmacol Ther. 2004;17(1)11-8.
El-Hashim AZ et al, "Nerve growth factor enhances cough via a central mechanism of action", Pharmacol Res. Aug. 2013;74:68-77. Epub Jun. 3, 2013.
EU Clinical Trial Register for Eudract No. 2006-002164-26, Oct. 9, 2006.

(Continued)

*Primary Examiner* — Michael Barker
(74) *Attorney, Agent, or Firm* — Silvia Salvadori, P.C.; Silvia Salvadori

(57) ABSTRACT

This invention relates to the new use of the compound 2-(R)-(4-Fluoro-2-methyl-phenyl)-4-(S)-((8aS)-6-oxo-hexahydro-pyrrolo[1,2-α]-pyrazin-2-yl)-piperidine-1-carboxylic acid [1-(R)-(3,5-bis-trifluoromethyl-phenyl)-ethyl]-methylamide (orvepitant) or pharmaceutically acceptable salts thereof and pharmaceutical compositions containing it and one or more therapeutic agents for the treatment of chronic cough, including chronic refractory cough and to combinations for such a use.

15 Claims, 1 Drawing Sheet

(56) References Cited

OTHER PUBLICATIONS

Fahy J.V., et al., "Effect of an NK1 receptor antagonist (CP-99,994) on hypertonic saline-induced bronchoconstriction and cough in male asthmatic subjects", Am J Respir Crit Care Med. Sep. 1995;152(3):879-84.
Faruqi S., et al., "On the definition of chronic cough and current treatment pathways: an international qualitative study", Cough. May 29, 2014;10:5. doi: 10.1186/1745-9974-10-5. eCollection 2014.
Gibson P., et al., "Treatment of Unexplained Chronic Cough: Chest Guideline and Expert Panel Report", Chest. Jan. 2016;149(1):27-44. Epub Jan. 6, 2016.
Gibson P.G., et al., "Management of chronic refractory cough", BMJ. Dec. 14, 2015;351:h5590.
Harle A.S.M., et al., "A placebo-controlled trial of aprepitant for cough in lung cancer", Journal of Clinical Oncology 2015 33:29_suppl, 2-2.
Harrison N.K., "Idiopathic pulmonary fibrosis: a nervous cough?", Pulm Pharmacol Ther. 2004;17(6):347-50.
Hope-Gill B.D., et al, "A Study of the Cough Reflex in Idiopathic Pulmonary Fibrosis", Am J Respir Crit Care Med. Oct. 15, 2003;168(8):995-1002. Epub Aug. 13, 2003.
Huang, et al., "Neurokinin-1 receptor antagonists: a comprehensive patent survey", Expert Opin Ther Pat. Aug. 2010;20(8):1019-45.
Irwin, R.S., et al., "Diagnosis and Management of Cough Executive Summary ACCP Evidence-Based Clinical Practice Guidelines", Chest, 2006; 129:1S-23S.
Joad J.P., et al., "Passive smoke effects on cough and airways in young guinea pigs: role of brainstem substance P", Am J Respir Crit Care Med. Feb. 15, 2004;169(4):499-504. Epub Nov. 25, 2003.
Katsumata U., et al., "Inhibitory actions of procaterol, a beta-2 stimulant, on substance P-induced cough in normal subjects during upper respiratory tract infection", Tohoku J Exp Med. May 1989;158(1):105-6.
Lavinka P.C. et al., "Molecular signaling and targets from itch: lessons for cough", Cough. 2013; 9: 8. Published online Mar. 6, 2013.
Lewis C.A., et al., "The Airways Pharmacology of DNK333, a Potent, Selective, Non-Peptide Dual NK1/NK2 Receptor Antagonist", Drug Development Research 2004;63:161-173.
Lim, K.G., et al., "Neuropeptide levels in nasal secretions from patients with and without chronic cough", Ann Allergy Asthma Immunol. Oct. 2011;107(4):360-3. Epub Sep. 8, 2011.
Mazzone S.B., et al., "Endogenous central suppressive mechanisms regulating cough as potential targets for novel antitussive therapies," Current Opinion in Pharmacology 2015, 22:1-8.
Mazzone S.B., et al., "Synergistic interactions between airway afferent nerve subtypes regulating the cough reflex in guinea-pigs", J. Physiol. Dec. 1, 2005;569(Pt 2):559-73. Epub Jul. 28, 2005.
Misery L., "Are Pruritus and Scratching the Cough of the Skin?", Dermatology. 2008;216(1):3-5.
Moreaux B., et al., "Role of substance P and tachykinin receptor antagonists in citric acid-induced cough in pigs", Eur J Pharmacol. Nov. 24, 2000;408(3):305-12.
Morice A.H., et al., "Expert opinion on the cough hypersensitivity syndrome in respiratory medicine," Eur Respir J 2014; 44: 1132-1148.
Morice A.H., et al., "Recommendations for the management of cough in adults", Thorax. Sep. 2006;61 Suppl 1:i1-24.
Munoz M., et al., "NK-1 receptor antagonists: a new paradigm in pharmacological therapy", Curr Med Chem. 2011;18(12):1820-31.
Mutolo D., et al., "Depression of cough reflex by microinjections of antitussive agents into caudal ventral respiratory group of the rabbit", J Appl Physiol (1985). Oct. 2010;109(4):1002-10. Epub Jul. 22, 2010.
Mutolo D., et al., "Modulation of the cough reflex by antitussive agents within the caudal aspect of the nucleus tractus solitarii in the rabbit", Am J Physiol Regul Integr Comp Physiol. Jul. 2008;295(1):R243-51. Epub May 14, 2008
Mutolo D., et al., "The role of excitatory amino acids and substance P in the mediation of the cough reflex within the nucleus tractus solitarii of the rabbit", Brain Res Bull. Sep. 28, 2007;74(4):284-93. Epub Jul. 23, 2007.
Otsuka K., et al., "Plasma substance P levels in patients with persistent cough", Respiration. 2011;82(5):431-8. Epub Aug. 12, 2011.
Patterson, R.N., et al., "Increased tachykinin levels in induced sputum from asthmatic and cough patients with acid reflux", Thorax. Jun. 2007;62(6):491-5. Epub Jan. 24, 2007.
Pavord I.D., et al., "Chronic Cough 2 Management of chronic cough", Lancet. Apr. 19, 2008;371(9621):1375-84.
Qiu Z., et al., "Cough reflex sensitivity and airway inflammation in patients with chronic cough due to non-acid gastro-oesophageal reflux", Respirology. May 2011;16(4):645-52.
Rolapitant NDA submission documents, Aug. 31, 2015.
Ryan N. M., et al., "Recent additions in the treatment of cough," J Thorac Dis 2014;6(S7):S739-S747.
Search Report and Written Opinion of International Patent Application PCT/EP2016/082698 of Mar. 24, 2017.
Sekizawa S., et al., "Distinct tachykinin NK1 receptor function in primate nucleus tractus solitarius neurons is dysregulated after second-hand tobacco smoke exposure", Br J Pharmacol. Jun. 2011; 163(4): 782-791.
Song W.J., et al., "Changing the paradigm for cough: does 'cough hypersensitivity' aid our understanding?", Asia Pac Allergy. Jan. 2014;4(1):3-13. Epub Jan. 31, 2014.
Song W.J., et al., "Cough hypersensitivity as a neuro-immune interaction", Clin Transl Allergy. Jul. 15, 2015;5:24., eCollection 2015.
Study of the Efficacy and Safety of SCH 619734 in Subjects with Chronic Idiopathic Cough, Oct. 2007.
Syed Y.Y., "Rolapitant: First Global Approval", Drugs. Nov. 2015;75(16):1941-5.
Ujiie Y, et al., "Evidence for Substance P as an Endogenous Substance Causing Cough in Guinea Pigs", Am Rev Respir Dis. Dec. 1993;148(6 Pt 1):1628-32.
Yang X.D., et al., "Regulatory effect of nerve growth factor on release of substance P in cultured dorsal root ganglion neurons of rat", Neurosci Bull. Jul. 2007;23(4):215-20.
Young E.C., et al, "Pharmacologic therapy for cough", Curr Opin Pharmacol. Jun. 2011;11(3):224-30.. Epub Jul. 1, 2011.
European Clinical Trial Register. (2014).
Richeldi L., et al., "Design of the Inpulsis trials: two phase 3 trials of nintedanib in patients with idiopathic pulmonary fibrosis", Respiratory Medicine (2014) 108, 1023-1030.
Van Manen M. JG, et al., "Cough in idiopathic pulmonary fibrosis", Eur Respir Rev. 2016; 25:278-286.

* cited by examiner

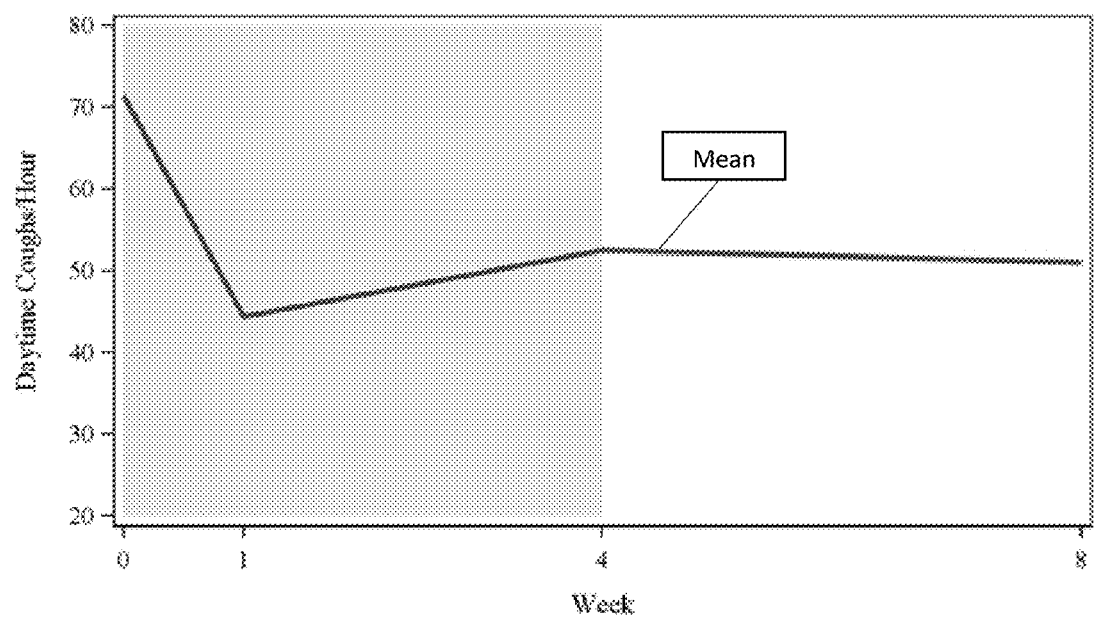
Figure 1. Objectively measured daytime cough frequency (absolute values).
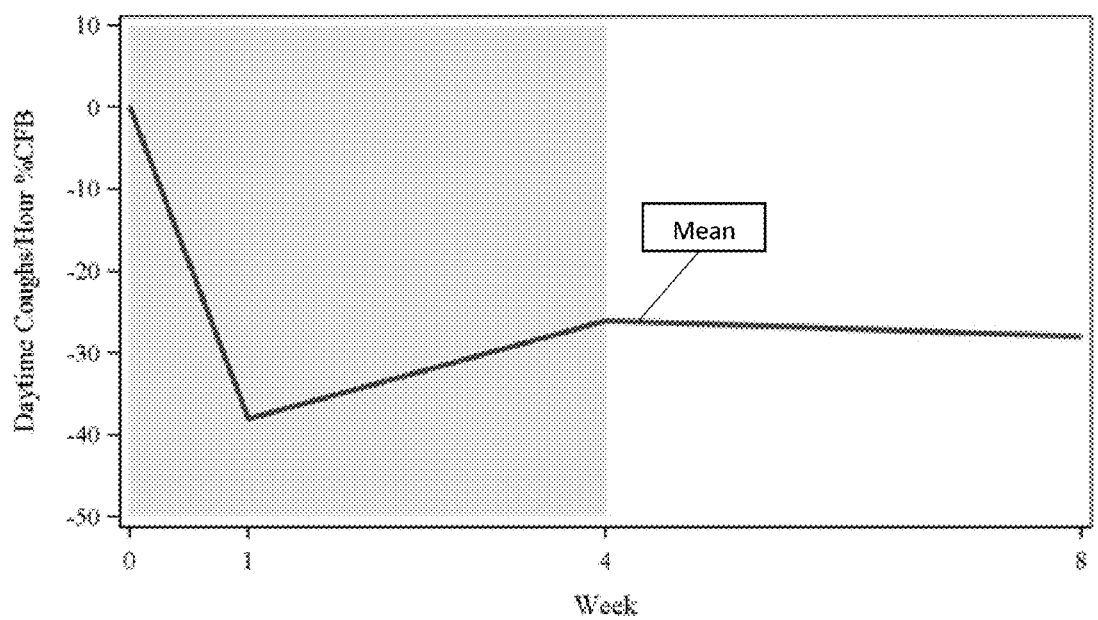
Figure 2. Objectively measured daytime cough frequency (% values).

METHOD OF TREATMENT OF CHRONIC COUGH ADMINISTERING ORVEPITANT IN COMBINATION WITH OTHER THERAPEUTIC AGENTS

This Non-Provisional Application is a continuation-in-part of U.S. Non-Provisional application Ser. No. 15/390,770, filed Dec. 27, 2016 which claims priority to and the benefit of U.S. Provisional Application No. 62/408,921. filed on Oct. 17, 2016 and of U.S. Provisional Application No. 62/276,237 filed on Jan. 8, 2016, the contents of which are all incorporated herein by reference in their entireties.

FIELD OF THE INVENTION

This invention relates to the new use of the compound 2-(R)-(4-Fluoro-2-methyl-phenyl)-4-(5)-((8aS)-6-oxo-hexahydro-pyrrolo[1,2-α]-pyrazin-2-yl)-piperidine-1-carboxylic acid [1-(R)-(3,5-bis-trifluoromethyl-phenyl)-ethyl]-methylamide (orvepitant) or pharmaceutically acceptable salts thereof and pharmaceutical compositions containing it for the treatment of chronic cough, including chronic refractory cough and to combinations for such a use.

BACKGROUND OF THE INVENTION

WO2003/066635 describes a number of diazabicycle derivatives as antagonists of tachykinin receptors, also known as substance P (SP) receptors or NK receptors and in particular NK-1 receptors, including the 2-(R)-(4-Fluoro-2-methyl-phenyl)-4-(S)-((8aS)-6-oxo-hexahydro-pyrrolo[1,2-α]-pyrazin-2-yl)-piperidine-1-carboxylic acid [1-(R)-(3,5-bis-trifluoromethyl-phenyl)-ethyl]-methylamide (otherwise known as orvepitant).

Orvepitant, otherwise known as 2-(R)-(4-Fluoro-2-methyl-phenyl)-4-(S)-((8aS)-6-oxo-hexahydro-pyrrolo[1,2-α]-pyrazin-2-yl)-piperidine-1-carboxylic acid [1-(R)-(3,5-bis-trifluoromethyl-phenyl)-ethyl]-methylamide has the following chemical structure (I).

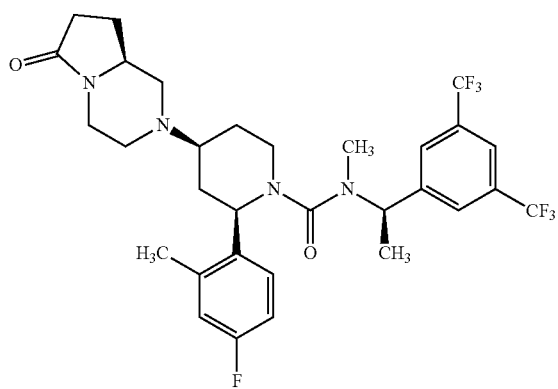

(I)

Hereinafter any reference to orvepitant refers to the compound (I).

Orvepitant may also be known as:

CAS Index name

1-Piperidinecarboxamide, N-[(1R)-1-[3,5-bis(trifluoromethyl)phenyl]ethyl]-2-(4-fluoro-2-methylphenyl)-4-[(8aS)-hexahydro-6-oxopyrrolo[1,2-α]pyrazin-2(1H)-yl]-N-methyl-, (2R,4S)

and

IUPAC name:

(2R,4S)—N-{(1R)-1-[3,5-bis(trifluoromethyl)phenyl]ethyl}-2-(4-fluoro-2-methylphenyl)-N-methyl-4-[(8aS)-6-oxohexahydropyrrolo[1,2-α]pyrazin-2(1H)-yl]-1-piperidinecarboxamide.

A preferred salt of the compound (I) is its hydrochloride salt which is otherwise known as orvepitant hydrochloride.

A further preferred salt of the compound (I) is its maleate salt which is otherwise known as orvepitant maleate.

WO2009/124996 describes a new crystalline form of orvepitant maleate namely anhydrous crystalline form (Form1).

The compound (I), pharmaceutically acceptable salts thereof are described in the aforementioned specifications as antagonists of tachykinin receptors, also known as substance P (SP) receptors or NK receptors and in particular NK-1 receptors, both in vitro and in vivo and are thus of use in the treatment of conditions mediated by tachykinins, including SP and other neurokinins.

Particularly, the compound (I), and pharmaceutically acceptable salts or solvates thereof are described as useful in the treatment of central nervous system (CNS) disorders.

We have now surprisingly found that the compound (I) or pharmaceutically acceptable salts thereof are also useful in the treatment of chronic cough.

Particularly, we have found that the compound (I) or pharmaceutically acceptable salts thereof are useful in the treatment of refractory chronic cough.

Refractory chronic cough also known as chronic refractory cough, chronic unexplained cough, chronic undiagnosed cough, chronic idiopathic cough, cough hypersensitivity syndrome, chronic intractable cough or chronic treatment-resistant cough is defined as a chronic cough of 8-weeks for which either no objective evidence of an underlying cause can be determined after routine clinical investigation or a cough that did not respond to standard treatment for the identified underlying cause.

Cough is a defensive reflex action of the respiratory system that is activated to clear the upper airways (Chung & Pavord, Lancet 2008; 371:1364-74). However, excessive coughing is the commonest reason for patients seeking medical care (Burt & Schappert, Vital and health statistics. Series 13, Data from the National Health Survey 2004; (157):1-70; Schappert & Burt, Series 13, Data from the National Health Survey 2006; (159):1-66) and has a significant impact on patient quality of life (French et al., Archives of internal medicine 1998; 158(15):1657-61; French et al., Chest 2005; 127(6):1991-8).

Coughing is most commonly associated with viral upper respiratory tract infections, where this symptom usually resolves spontaneously within a 3 week period. Chronic coughing (in which persists in a troublesome form for more than eight weeks duration) however may affect up to 12% of the UK population (Ford et al., Thorax 2006; 61(11):975-9) and 18% of the US (Barbee et al., Chest. 1991; 99(1):20-6), afflicts women more often than men and generally has an onset from middle age (Ford et al., Thorax 2006; 61(11): 975-9; Irwin et al., The American review of respiratory disease 1981; 123(4 Pt 1):413-7; Irwin et al., Chest 2006; 129(1 Suppl):1S-23S; Janson et al., The European respiratory journal: official journal of the European Society for Clinical Respiratory Physiology 2001; 18(4):647-54).

Chronic coughing may be associated with many conditions including interstitial lung diseases (also called parenchymal diseases) such as: emphysema, idiopathic pulmonary fibrosis (IPF) and sarcoidosis; airway diseases such as asthma, chronic bronchitis, chronic postnasal drip, eosinophilic bronchitis and chronic obstructive pulmonary disease; chronic infections such as: bronchiectasis, tuberculosis, cystic fibrosis; lung tumours such as: bronchogenic carcinoma, alveolar cell carcinoma, benign airway tumours, mediastinal tumours; cardiovascular disease such as: left ventricular failure, pulmonary infarction, aortic aneurysm; other diseases such as: reflux oesophagitis, recurrent aspiration, endobronchial sutures, postnasal drip syndrome or rhinosinusitis; drug related such as: administration of angiotensin-converting enzyme inhibitors (Chung & Pavord, Lancet 2008; 371:1364-74).

Chronic coughing has been shown to have significant physical, social and psychological consequences (Birring et al., Thorax 2003; 58(4):339-43; French et al., Chest 2002; 121(4):1123-31). Patients often suffer complications such as chest and abdominal pains, retching and vomiting, urinary incontinence and even cough syncope. Many are embarrassed and stigmatised by this symptom and therefore avoid public places and social gatherings. Depression scores in this patient population have been found to be comparable to those seen in other serious chronic illnesses such as rheumatoid arthritis and sickle cell disease (Dicpinigaitis et al., Chest 2006; 130(6):1839-43).

Clinicians cannot identify a treatable cause for chronic cough in about 40% of patients (Hague et al., Chest 2005; 127(5):1710-3); as a result the treatment options for these chronic treatment-refractory cough patients are very limited (Gibson & Vertigan, BMJ. 2015; 351:h5590). To date the only drug therapies that have been shown to be effective in randomised controlled trials in this patient group are morphine (Morice et al., American journal of respiratory and critical care medicine 2007; 175(4):312-5) and gabapentin (Ryan et al., Lancet. 2012; 380(9853):1583-9). Other studies have suggested treatments such as amitriptyline and pregabalin (Halum et al., The Laryngoscope 2009; 119(9): 1844-7) may be of help, but all these available pharmacological treatment choices are frequently associated with intolerable side effects such as drowsiness, tiredness, gastrointestinal disturbances, and some of these agents, such as for example morphine, are also addictive.

Thus there is an urgent need to identify new, effective and well-tolerated therapies for this debilitating condition to alleviate patient suffering.

SUMMARY OF THE INVENTION

The solution provided by the present invention is the use of the 2-(R)-(4-Fluoro-2-methyl-phenyl)-4-(S)-((8aS)-6-oxo-hexahydro-pyrrolo[1,2-α]-pyrazin-2-yl)-piperidine-1-carboxylic acid [1-(R)-(3,5-bis-trifluoromethyl-phenyl)-ethyl]-methylamide (otherwise known as orvepitant) having the following chemical structure (I)

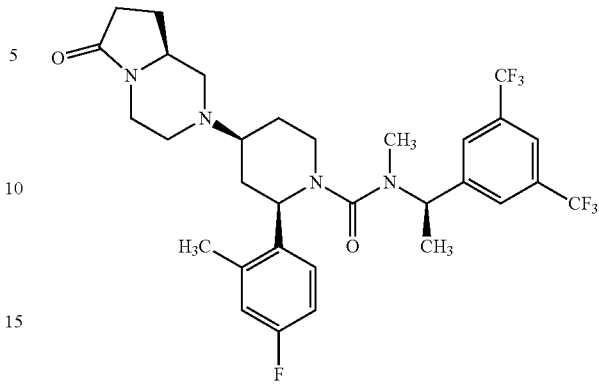

or pharmaceutically acceptable salts thereof in the treatment of chronic cough.

In a first aspect, the invention provides a method of treatment of chronic cough which comprises administering to a human in need thereof an effective amount 2-(R)-(4-Fluoro-2-methyl-phenyl)-4-(S)-((8aS)-6-oxo-hexahydro-pyrrolo[1,2-α]-pyrazin-2-yl)-piperidine-1-carboxylic acid [1-(R)-(3,5-bis-trifluoromethyl-phenyl)-ethyl]-methylamide (orvepitant) or a pharmaceutically acceptable salt thereof.

In a further aspect, the invention provides a method of treatment of chronic refractory cough which comprises administering to a human in need thereof an effective amount 2-(R)-(4-Fluoro-2-methyl-phenyl)-4-(S)-((8aS)-6-oxo-hexahydro-pyrrolo[1,2-α]-pyrazin-2-yl)-piperidine-1-carboxylic acid [1-(R)-(3,5-bis-trifluoromethyl-phenyl)-ethyl]-methylamide(orvepitant) or a pharmaceutically acceptable salt thereof.

In another aspect the invention provides a pharmaceutical composition comprising 2-(R)-(4-Fluoro-2-methyl-phenyl)-4-(S)-((8aS)-6-oxo-hexahydro-pyrrolo[1,2-α]-pyrazin-2-yl)-piperidine-1-carboxylic acid [1-(R)-(3,5-bis-trifluoromethyl-phenyl)-ethyl]-methylamide (orvepitant) or a pharmaceutically acceptable salt thereof for use in the treatment of chronic cough.

In another aspect the invention provides a pharmaceutical composition comprising 2-(R)-(4-Fluoro-2-methyl-phenyl)-4-(S)-((8aS)-6-oxo-hexahydro-pyrrolo[1,2-α]-pyrazin-2-yl)-piperidine-1-carboxylic acid [1-(R)-(3,5-bis-trifluoromethyl-phenyl)-ethyl]-methylamide (orvepitant) or a pharmaceutically acceptable salt thereof for use in the treatment of chronic refractory cough.

In one embodiment, the maleate salt of orvepitant is utilized in the treatment of chronic cough including chronic refractory cough.

In a further embodiment, orvepitant maleate Form 1 is utilized in the treatment of chronic cough, including chronic refractory cough.

BRIEF DESCRIPTION OF THE DRAWINGS

FIG. 1. Objectively measured daytime cough frequency (absolute values). Legend: Baseline=Week 0. Week 4 is end to treatment period. Week 8 is the Follow-up visit. FIG. 2. Objectively measured daytime cough frequency (% values). Legend: % CFB=Percent Change from Baseline (Week 0). Week 4 is end of treatment period. Week 8 is the Follow-up visit.

DETAILED DESCRIPTION OF THE INVENTION

The present invention relates to the use of 2-(R)-(4-Fluoro-2-methyl-phenyl)-4-(S)-((8aS)-6-oxo-hexahydro-pyrrolo[1,2-α]-pyrazin-2-yl)-piperidine-1-carboxylic acid [1-(R)-(3,5-bis-trifluoromethyl-phenyl)-ethyl]-methylamide or a pharmaceutically acceptable salt or a solvate thereof for the manufacture of a medicament for the treatment of chronic cough.

2-(R)-(4-Fluoro-2-methyl-phenyl)-4-(S)-((8aS)-6-oxo-hexahydro-pyrrolo[1,2-α]-pyrazin-2-yl)-piperidine-1-carboxylic acid [1-(R)-(3,5-bis-trifluoromethyl-phenyl)-ethyl]-methylamide (otherwise known as orvepitant) has the following chemical structure (I).

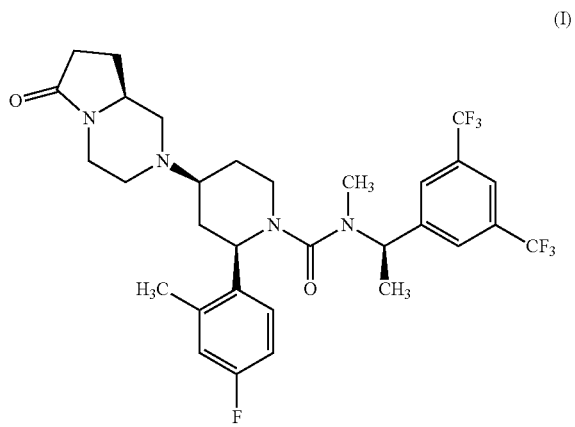 [SMILES: Cc1cc(F)ccc1[C@H]1C[C@@H](N2CCN3C(=O)CC[C@H]3C2)CCN1C(=O)N(C)[C@H](C)c1cc(C(F)(F)F)cc(C(F)(F)F)c1]

(I)

The compound (I) or its pharmaceutically acceptable salts may be prepared by the processes described in International patent applications no. WO2003/066635, WO2009/124996 and WO2007/048642, which are incorporated herein by reference.

Specifically, the Examples 9a and 11 of WO2003/066635 describe the synthesis of the compound (I) as free base and as hydrochloride salt respectively. Specific crystalline forms of hydrochloride salt namely anhydrous and dihydrate crystalline forms are described in the Examples 11a and 11b respectively. Example 11c describes the synthesis of the compound (I) as a maleate salt. Examples 2-8 of WO2009/124996 describe the synthesis of the maleate salt of the compound (I) as anhydrous crystalline form (Form1).

Orvepitant maleate Form 1 is characterized by X-ray powder diffraction (XRD) pattern expressed in terms of 2 theta angles and obtained with a diffractometer using copper Kα X-radiation, wherein the XRD pattern comprises 2 theta angle peaks at essentially at 7.3±0.1, 7.5±0.1, 10.9±0.1, 12.7±0.1, 16.5±0.1 degrees, which correspond respectively to d-spacings at 12.2, 11.8, 8.1, 7.0 and 5.4 Angstroms (Å).

Example 1 of WO2007/048642 discloses a process for preparing an intermediate in the synthesis of the compound (I).

It will be appreciated that for use in medicine, the salts of the compound (I) should be pharmaceutically acceptable. Suitable pharmaceutically acceptable salts will be apparent to those skilled in the art and include for example acid addition salts formed with pharmaceutically acceptable organic or inorganic acids. Examples of salts include hydrochloride, hydrobromide, sulphate, alkyl- or arylsulphonate e.g. methanesulphonate otherwise known as mesylates or p-toluenesulphonate (otherwise known as tosylate), phosphate, acetates, citrate, succinate, tartrate, fumarate and maleate.

One such pharmaceutically acceptable salt of the compound (I) for use according to the present invention is the maleate salt (orvepitant maleate).

Certain salts of the compound (I) may exist in stereoisomeric forms (e.g. they may contain one or more asymmetric carbon atoms). The individual stereoisomers (enantiomers and diastereomers) and mixtures of these are included within the scope of the present invention. Likewise, it is understood that salts of the compound (I) may exist in tautomeric forms and these are also included within the scope of the present invention.

The compound (I) may form acid addition salts with one or more equivalents of the acid. The present invention may employ all possible stoichiometric and non-stoichiometric forms thereof in the formulations of the invention.

The compound (I) or pharmaceutically acceptable salts thereof may exist in the form of a solvate.

It will be appreciated that many organic compounds can form complexes with solvents in which they are reacted or from which they are precipitated or crystallised. These complexes are known as "solvates". For example, a complex with water is known as a "hydrate". Solvents with high boiling points and/or solvents with a high propensity to form hydrogen bonds such as water, ethanol, iso-propyl alcohol, and N-methyl pyrrolidinone may be used to form solvates. Methods for the identification of solvated include, but are not limited to, NMR and microanalysis.

The compound (I) or pharmaceutically acceptable salts thereof may exist in different polymorphic forms.

Polymorphism is defined as the ability of an element or compound to crystallise in more than one distinct crystalline phase. Thus, polymorphs are distinct solids sharing the same molecular formula, however since the properties of any solid depends on its structure, different polymorphs may exhibit distinct physical properties such as different solubility profiles, different melting points, different dissolution profiles, different thermal and/or photostability, different shelf life, different suspension properties and different physiological absorption rate. Inclusion of a solvent in the crystalline solid leads to solvates, and in the case of water as a solvent, hydrates.

Included within the compound (I) are all solvates (including hydrates) and polymorphs of the compound (I) or pharmaceutically acceptable salts thereof.

The compound (I) or pharmaceutically acceptable salts or solvates thereof has now been determined to be useful in the treatment of chronic cough.

In one embodiment of the invention, the compound for use according to the present invention is 2-(R)-(4-Fluoro-2-methyl-phenyl)-4-(S)-((8aS)-6-oxo-hexahydro-pyrrolo[1,2-α]-pyrazin-2-yl)-piperidine-1-carboxylic acid [1-(R)-(3,5-bis-trifluoromethyl-phenyl)-ethyl]-methylamide maleate (orvepitant maleate).

In one embodiment of the invention, the compound for use according to the present invention is 2-(R)-(4-Fluoro-2-methyl-phenyl)-4-(S)-((8aS)-6-oxo-hexahydro-pyrrolo[1,2-α]-pyrazin-2-yl)-piperidine-1-carboxylic acid [1-(R)-(3,5-bis-trifluoromethyl-phenyl)-ethyl]-methylamide maleate as anhydrous crystalline form (Form 1) (orvepitant maleate Form 1).

Definitions

All numbers expressing quantities, percentages or proportions, and other numerical values used in the specification and claims, are to be understood as being modified in all instances by the term "about."

It should be understood that the terms "a" and "an" as used herein refer to "one or more" of the enumerated components. It will be clear to one of ordinary skill in the art that the use of the singular includes the plural unless specifically stated otherwise.

As used herein, the terms "treatment," "treating," and the like, refer to obtaining a desired pharmacologic, physiologic, dermatologic or cosmetic effect. The effect may be prophylactic in terms of completely or partially preventing a condition or disease or disorder or symptom thereof and/or may be therapeutic in terms of a partial or complete cure for a condition or disease or disorder and/or adverse symptom or effect attributable to the condition or disease or disorder.

"Treatment," thus, for example, covers any treatment of a condition or disease in a mammal, particularly in a human, and includes: (a) preventing the condition or disease, disorder or symptom thereof from occurring in a subject which may be predisposed to the condition or disease or disorder but has not yet been diagnosed as having it; (b) inhibiting the condition or disease, disorder or symptom thereof, such as, arresting its development; and (c) relieving, alleviating or ameliorating the condition or disease or disorder or symptom thereof, such as, for example, causing regression of the condition or disease or disorder or symptom thereof.

As used herein, the term "effective amount" means that amount of a drug or pharmaceutical agent that will elicit the biological or medical response of a tissue, system, animal or human that is being sought, for instance, by a researcher, clinician or veterinarian.

The term "chronic cough" refers to cough which persists in a troublesome form for more than eight weeks as defined in treatment guidelines from the British Thoracic Society (Morice et al., Thorax. 2006 September; 61 Suppl 1:i1-24) and the American College of Physicians (Irwin et al., Chest. 2006 January; 129(1 Suppl):1S-23S).

As used herein, the term "refractory chronic cough" refers to cough which persists in a troublesome form for more than eight weeks and for which there is either no objective evidence of an underlying cause as determined after routine clinical investigation or a cough that did not respond to standard treatment for the identified underlying cause (Gibson & Vertigan, BMJ. 2015; 351:h5590).

As used herein, the term "chronic refractory cough" is interchangeable with the terms "refractory chronic cough", "chronic unexplained cough", "chronic undiagnosed cough", "chronic idiopathic cough", "cough hypersensitivity syndrome", or "chronic treatment-resistant cough" and is intended to have the same meaning.

As used herein, "pharmaceutically acceptable excipient" or "pharmaceutically acceptable carrier" mean a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be pharmaceutically-acceptable e.g. of sufficiently high purity.

The term "combination" as used herein refers to either a fixed combination in one dosage unit form, or non-fixed combination.

The term "fixed combination" means that the active ingredients, e.g. a compound of formula (I) or pharmaceutically acceptable salt thereof and a combination partner, are both administered to a patient simultaneously in the form of a single entity or dosage.

The term "non-fixed combination" means that the active ingredients, e.g. a compound (I) or pharmaceutically acceptable salt thereof and a combination partner, (e.g. another drug as explained below, also referred to as "therapeutic agent" or "co-agent") are both administered to a patient as separate entities either simultaneously, concurrently or sequentially with no, specific time limits, wherein such administration provides therapeutically effective levels of the two compounds in the body of the patient. The latter also applies to cocktail therapy, e.g., the administration of three or more active ingredients.

The terms "co-administration" or "combined administration" or the like as utilized herein are meant to encompass administration of the compound (I) and the selected combination partner to a single subject in need thereof (e.g. a patient), and are intended to include treatment regimens in which the agents are not necessarily administered by the same route of administration or at the same time.

The patient to be treated using the invention described herein is preferably a human.

In one embodiment of the present invention, chronic cough is refractory chronic cough.

Chronic cough is a common symptom in people who develop interstitial lung diseases (ILDs) (Brown, 2006; 129(1 Suppl):180S-185S).

The term interstitial lung diseases (ILDs), also known as diffuse parenchymal lung disease (DPLD), refers to a group of lung diseases affecting the interstitium (the tissue and space around the air sacs of the lungs).

The interstitium is a lace-like network of tissue that extends throughout both lungs. The interstitium provides support to the lungs' microscopic air sacs (alveoli). Tiny blood vessels travel through the interstitium, allowing gas exchange between blood and the air in the lungs. Normally, the interstitium is so thin it cannot be seen on chest X-rays or computerised tomography (CT) scans.

All forms of ILD cause thickening of the interstitium. The thickening can be due to inflammation, scarring, or extra fluid (edema). Some forms of ILD are short-lived; others are chronic and irreversible.

ILDs include idiopathic pulmonary fibrosis (IPF), a chronic, progressive form of fibrosis (scarring) of the interstitium. Cough is estimated to be present in 84% of patients with IPF, is more prevalent in patients who have never smoked or who have more advanced disease and is an independent predictor of disease progression (Ryerson et al., Respirology 2011; 16:969-75). IPF is a progressive and usually fatal course with a medium survival of 2-3 years following diagnosis; its cause is unknown. Patients with IPF are usually between 50 to 70 years old and the incidence is lower in women (7.4 cases per 100,000 per year) then men (10.7 cases per 100,000 per year). The incidence, prevalence and death increase with age. At present, no pharmacological therapy is able to cure the disease and most treatment strategies have been based on eliminating or suppressing the inflammatory component though the condition responds poorly to immunosuppressive therapies. Recently however two drugs with anti-fibrotic activity, pirfenidone and nintedanib, have been shown in placebo controlled clinical trials to slow, but not halt disease progression.

ILDs may also include:
- Idiopathic interstitial pneumonias (IPP) such as nonspecific interstitial pneumonia, desquamative interstitial pneumonia, acute interstitial pneumonia, cryptogenic organizing pneumonia, lymphoid interstitial pneumonia, combined pulmonary fibrosis and emphysema syndrome (CPFE);
- Environmental and occupational diseases that are due to hypersensitivity for example: pneumoconiosis such as asbestosis, silicosis, and due to coal dust, beryllium, hard metal dust exposure, and extrinsic allergic alveolitis for example 'bird fancier's lung, radiation fibrosis syndrome, or due to exposure to bacteria and molds such as with mycoplasma pneumonia;
- Multi-system diseases that are associated with autoimmune diseases for example: connective tissue diseases such as systemic sclerosis, sarcoidosis, rheumatoid arthritis, Wegener's granulomatosis; certain muscle diseases such as polymyositis, dermatomyositis, and the anti-synthetase syndrome, or as a result of drug reactions for example with amiodarone, methotrexate and bleomycin;
- Rare lung diseases for example: pulmonary alveolar proteinosis, pulmonary histiocytosis, pulmonary eosinophilia and idiopathic pulmonary haemosiderosis, Hermansky-Pudlak syndrome, tuberose sclerosis (lymphangioleiomyomatosis);
- Genetic or inherited diseases for example: familial pulmonary fibrosis (FPF) or familial interstitial pneumonia (FIP);
- Bronchiolitis Obliterans Syndrome following lung transplantation.

Treatment of chronic cough in interstitial lung diseases (ILDs) remains problematic for both patients and physicians, and it may be associated with severe breathlessness. In such cases, palliative therapy using conventional antitussive agents such as opiate-derived preparations often proves to be of limited benefit.

Thus, according to a further embodiment of the present invention, chronic cough is due or associated with interstitial lung diseases (ILDs).

In another embodiment, the present invention provides a method of treatment of chronic cough due or associated with sarcoidosis, emphysema or IPF comprising administering to a human in need thereof a therapeutically effective amount of the compound of formula (I) or pharmaceutically acceptable salts thereof.

In another embodiment, the present invention provides a method of treatment of chronic cough due or associated with sarcoidosis, comprising administering to a human in need thereof a therapeutically effective amount of the compound of formula (I) or pharmaceutically acceptable salts thereof.

In another embodiment, the present invention provides a method of treatment of chronic cough due or associated with emphysema comprising administering to a human in need thereof a therapeutically effective amount of the compound of formula (I) or pharmaceutically acceptable salts thereof.

In another embodiment, the present invention provides a method of treatment of chronic cough due or associated with pulmonary fibrosis comprising administering to a human in need thereof a therapeutically effective amount of the compound of formula (I) or pharmaceutically acceptable salts thereof.

In another embodiment, the present invention provides a method of treatment of chronic cough due or associated with IPF comprising administering to a human in need thereof a therapeutically effective amount of the compound of formula (I) or pharmaceutically acceptable salts thereof.

Chronic cough is also a common symptom in people who develop airway diseases such as asthma, chronic bronchitis, chronic postnasal drip, eosinophilic bronchitis and chronic obstructive pulmonary disease; chronic infections such as: bronchiectasis, tuberculosis, cystic fibrosis; lung tumours such as: bronchogenic carcinoma, alveolar cell carcinoma, benign airway tumours, mediastinal tumours; cardiovascular disease such as: left ventricular failure, pulmonary infarction, aortic aneurysm; other diseases such as: reflux oesophagitis, recurrent aspiration, endobronchial sutures, postnasal drip syndrome or rhinosinusitis; drug related such as: administration of angiotensin-converting enzyme inhibitors: other diseases such as: reflux oesophagitis, recurrent aspiration, endobronchial sutures, postnasal drip syndrome or rhinosinusitis; drug related such as: administration of angiotensin-converting enzyme inhibitors.

Thus, according to a further embodiment of the present invention, chronic cough is due or associated with asthma, chronic bronchitis, chronic postnasal drip, eosinophilic bronchitis and chronic obstructive pulmonary disease.

In a further embodiment, the present invention provides a method of treatment of chronic cough due or associated with asthma, chronic bronchitis, chronic postnasal drip, eosinophilic bronchitis and chronic obstructive pulmonary disease, comprising administering to a human in need thereof a therapeutically effective amount of the compound of formula (I) or pharmaceutically acceptable salts thereof.

Thus, according to a further embodiment of the present invention, chronic cough is due or associated with chronic infections such as bronchiectasis, tuberculosis, cystic fibrosis.

In a further embodiment, the present invention provides a method of treatment of chronic cough due or associated with chronic infections such as bronchiectasis, tuberculosis, cystic fibrosis, comprising administering to a human in need thereof a therapeutically effective amount of the compound of formula (I) or pharmaceutically acceptable salts thereof.

Thus, according to a further embodiment of the present invention, chronic cough is due or associated with lung tumours such as bronchogenic carcinoma, alveolar cell carcinoma, benign airway tumours, mediastinal tumours.

In a further embodiment, the present invention provides a method of treatment of chronic cough due or associated with lung tumours such as bronchogenic carcinoma, alveolar cell carcinoma, benign airway tumours, mediastinal tumours, comprising administering to a human in need thereof a therapeutically effective amount of the compound of formula (I) or pharmaceutically acceptable salts thereof.

Thus, according to a further embodiment of the present invention, chronic cough is due or associated with a cardiovascular disease such as left ventricular failure, pulmonary infarction, aortic aneurysm.

In a further embodiment, the present invention provides a method of treatment of chronic cough due or associated with cardiovascular disease such as left ventricular failure, pulmonary infarction, aortic aneurysm, comprising administering to a human in need thereof a therapeutically effective amount of the compound of formula (I) or pharmaceutically acceptable salts thereof.

Thus, according to a further embodiment of the present invention, chronic cough is due or associated with reflux oesophagitis, recurrent aspiration, endobronchial sutures, postnasal drip syndrome or rhinosinusitis.

In a further embodiment, the present invention provides a method of treatment of chronic cough due or associated with reflux oesophagitis, recurrent aspiration, endobronchial sutures, postnasal drip syndrome or rhinosinusitis, comprising administering to a human in need thereof a therapeutically effective amount of the compound of formula (I) or pharmaceutically acceptable salts thereof.

In a further embodiment, the present invention provides a method of treatment of chronic cough due or associated with sarcoidosis, emphysema or idiopathic pulmonary fibrosis (IPF), with asthma, chronic bronchitis, chronic postnasal drip, eosinophilic bronchitis and chronic obstructive pulmonary disease (COPD), with chronic infections such as bronchiectasis, tuberculosis, cystic fibrosis, with lung tumours such as bronchogenic carcinoma, alveolar cell carcinoma, benign airway tumours, mediastinal tumours, or with cardiovascular disease such as left ventricular failure, pulmonary infarction, aortic aneurysm, which comprises administering to a human in need thereof an effective amount of 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) or a pharmaceutically acceptable salt thereof.

In a further embodiment, the present invention provides a method of treatment of chronic cough due or associated with idiopathic pulmonary fibrosis (IPF), with lung tumours such as bronchogenic carcinoma, alveolar cell carcinoma, benign airway tumours, mediastinal tumours or with chronic obstructive pulmonary disease (COPD) which comprises administering to a human in need thereof an effective amount of 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) or a pharmaceutically acceptable salt thereof.

Further, the compound of formula (I) and salts thereof are suitable for use in a method of treating of Interstitial lung diseases (ILDs), particularly in treating pulmonary fibrosis such as idiopathic pulmonary fibrosis (IPF).

Thus, in a further aspect, the invention provides a method of treatment of ILDs which comprises administering to a human in need thereof an effective amount of 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) or a pharmaceutically acceptable salt thereof.

In a yet further aspect, the invention provides a method of treatment of ILDs which comprises administering to a human in need thereof an effective amount of 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) maleate.

In a yet further aspect, the invention provides a method of treatment of ILDs which comprises administering to a human in need thereof an effective amount of 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) maleate as anhydrous crystalline form (Form1).

Moreover, in a still further aspect provided is a method for treatment of IPF comprising administering to a human in need thereof a therapeutically effective amount of 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) or a pharmaceutically acceptable salt thereof.

Moreover, in a still further aspect provided is a method for treatment of IPF comprising administering to a human in need thereof a therapeutically effective amount of 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) maleate.

Moreover, in a still further aspect provided is a method for treatment of pulmonary fibrosis, such as IPF comprising administering to a human in need thereof a therapeutically effective amount of 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) maleate as anhydrous crystalline form (Form1).

In one embodiment, the human is a paediatric patient.

Pharmaceutical compositions for use in accordance with the present invention may be formulated in a conventional manner for use in human and veterinary medicine using one or more pharmaceutically acceptable carriers or excipients.

Thus, the compound (I) and its pharmaceutically acceptable salts may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or formulated in conventional manner.

The compound (I) or its pharmaceutically acceptable salts may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compound (I) or its pharmaceutically acceptable salts can be formulated for dermal administration.

Dermal administration may include topical application or transdermal administration. Transdermal application can be accomplished by suitable patches, emulsions, ointments, solutions, suspensions, pastes, foams, aerosols, lotions, creams or gels as is generally known in the art, specifically designed for the transdermal delivery of active agents, optionally in the presence of specific permeability enhancers. Topical compositions can likewise take one or more of these forms. One or more active compounds may be present in association with one or more non-toxic pharmaceutically acceptable auxiliaries such as excipients, adjuvants (e.g. buffers), carriers, inert solid diluents, suspending agents, preservatives, fillers, stabilizers, anti-oxidants, food additives, bioavailability enhancers, coating materials, granulating and disintegrating agents, binding agents etc., and, if desired, other active ingredients.

The pharmaceutical composition may be formulated, for example, for immediate release, sustained release, pulsed release, two or more step release, or depot or any other kind of release.

The manufacture of the pharmaceutical compositions according to the present subject matter may be performed according to methods known in the art and will be explained in further detail below. Commonly known and used pharmaceutically acceptable auxiliaries as well as further suitable diluents, flavorings, sweetening agents, coloring agents etc. may be used, depending on the intended mode of administration as well as particular characteristics of the active compound to be used, such as solubility, bioavailability etc.

Any non-toxic, inert, and effective topical, oral, etc. pharmaceutically acceptable carrier may be used to formulate the compositions described herein. Well-known carriers used to formulate other topical therapeutic compositions for administration to humans are useful in these compositions. Examples of these components that are well known to those of skill in the art are described in *The Merck Index*, Thirteenth Edition, Budavari et al., Eds., Merck & Co., Inc., Rahway, N.J. (2001); the CTFA (Cosmetic, Toiletry, and Fragrance Association) *International Cosmetic Ingredient Dictionary and Handbook*, Tenth Edition (2004); and the "Inactive Ingredient Guide", U.S. Food and Drug Administration (FDA) Center for Drug Evaluation and Research (CDER) Office of Management, January 1996, the contents of which are hereby incorporated by reference in their entirety. Examples of such useful cosmetically acceptable excipients, carriers and diluents include distilled water, physiological saline, Ringer's solution, dextrose solution, Hank's solution, and DMSO, which are among those suitable for use herein.

These additional other inactive components, as well as effective formulations and administration procedures, are well known in the art and are described in standard textbooks, such as *Goodman and Gillman's: The Pharmacological Bases of Therapeutics*, 8th Ed., Gilman et al. Eds. Pergamon Press (1990) and *Remington's Pharmaceutical Sciences*, 17th Ed., Mack Publishing Co., Easton, Pa. (1990), both of which are incorporated by reference herein in their entirety.

In an embodiment, the present topical compositions are formulated in a serum, a gel cream, a lotion, a cream, an ointment, a gel, an aerosol, a foam, a foamable liquid, a solution (solubilized system), a paste, a suspension, a dispersion, an emulsion, a skin cleanser, a milk, a mask, a solid stick, a bar (such as a soap bar), an encapsulated formulation, a microencapsulated formulation, microspheres or nanospheres or vesicular dispersions, or other cosmetically acceptable topical dosage form. In the case of vesicular dispersions, the vesicles may be composed of lipids, which can be of the ionic or nonionic type, or a mixture thereof. The formulation can comprise one or more of an aqueous formulation and/or an anhydrous formulation.

In another embodiment, the present topical cosmetic composition in accordance with the subject matter described herein can comprise or consist of an anhydrous formulation, an aqueous formulation, or an emulsion.

For intranasal administration, the compound (I) or its pharmaceutically acceptable salts may be formulated as solutions for administration via a suitable metered or unitary dose device or alternatively as a powder mix with a suitable carrier for administration using a suitable delivery device.

A proposed dose of the compound (I) is approximately 0.5 to 30 mg per day. Preferably, it is 1 to 30 mg per day, more preferably 2.5 to 30 mg per day.

In one embodiment, the dose of the compound (I) is 10 mg per day, 20 mg per day or 30 mg per day.

It will be appreciated that it may be necessary to make routine variations to the dosage, depending on the age and condition of the patient and the precise dosage will be ultimately at the discretion of the attendant physician or veterinarian. The dosage will also depend on the route of administration.

If desired, other therapeutic agents can be employed in conjunction with those provided in the above-described compositions. The amount of active ingredients that may be combined with the carrier materials to produce a single dosage form will vary depending upon the host treated, the nature of the disease, disorder, or condition, and the nature of the active ingredients.

The pharmaceutical compositions of the present invention may be given in a single dose or multiple doses daily.

In one embodiment, the compound (I) and its pharmaceutically acceptable salts is administered orally once daily.

In an embodiment, the present compositions may be topically applied once or multiple times per day. In an embodiment, the present compositions are topically applied from one to four times daily. For example, starting with once daily and progressing to more frequent applications, if needed, is one strategy.

In an embodiment, the present compositions are topically applied from one to six times daily, for example, in the morning, at noon, in the afternoon, and/or in the evening.

It is understood, however, that a specific dose level for any particular patient will vary depending upon a variety of factors, including the activity of the specific active agent; the age, body weight, general health, sex and diet of the patient; the time of administration; the rate of excretion; possible drug combinations; the severity of the particular condition being treated; and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time are well known in the art.

The optimal formulations can be determined by one skilled in the art depending upon considerations such as the particular ingredients and the desired dosage. See, for example, *Remington's Pharmaceutical Sciences*, 18th ed. (1990, Mack Publishing Co., Easton, Pa. 18042), pp. 1435-1712, and "Harry's Cosmeticology", 8th ed. (2000, Chemical Publishing Co., Inc., New York, N.Y. 10016), the disclosure of each of which is hereby incorporated by reference herein in its entirety. Such formulations may influence the physical state, stability, rate of in vivo release, and rate of in vivo clearance.

In particular, the ability to formulate compositions capable of long term storage, without pre-mixing or compounding requirements prior to application, are also contemplated. Specifically, the present compositions remain unexpectedly stable in storage for periods including between about 3 months and about 3 years, about 3 months and about 2.5 years, between about 3 months and about 2 years, between about 3 months and about 20 months, and alternately any time period between about 6 months and about 18 months.

Thus, in another aspect, the invention provides a pharmaceutical composition comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) or a pharmaceutically acceptable salt thereof for use in the treatment of chronic cough.

In another embodiment, the invention provides a pharmaceutical composition comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) maleate, for use in the treatment of chronic cough.

In another embodiment, the invention provides a pharmaceutical composition comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) maleate as anhydrous crystalline form (Form1) for use in the treatment of chronic cough.

In another embodiment, the invention provides a pharmaceutical composition comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) maleate, for use in the treatment of refractory chronic cough.

In a further embodiment, the invention provides a pharmaceutical composition comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) or a pharmaceutically acceptable salt thereof for use in the treatment of refractory chronic cough.

In another embodiment, the invention provides a pharmaceutical composition comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide(orvepitant) maleate as anhydrous crystalline form (Form1) for use in the treatment of refractory chronic cough.

In another embodiment, the invention provides a pharmaceutical composition for oral administration comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) or a pharmaceutically acceptable salt thereof, for use in the treatment of ILDs.

In another embodiment, the invention provides a pharmaceutical composition for oral administration comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate (orvepitant) or a pharmaceutically acceptable salt thereof, for use in the treatment of IPF.

In another embodiment, the invention provides a pharmaceutical composition for oral administration comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) maleate, for use in the treatment of ILDs.

In another embodiment, the invention provides a pharmaceutical composition for oral administration comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) maleate for use in the treatment of IPF.

In another embodiment, the invention provides a pharmaceutical composition for oral administration comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide(orvepitant) maleate as anhydrous crystalline form (Form1) for use in the treatment of ILDs.

In another embodiment, the invention provides a pharmaceutical composition for oral administration comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate as anhydrous crystalline form (Form1) for use in the treatment of IPF.

It will be appreciated by those skilled in the art that the compound (I) or pharmaceutically acceptable salts thereof according to the invention may advantageously be used in combination with one or more other therapeutic agents, for instance with leukotriene receptor antagonists such as montelukast and zafirlukast; voltage-gated sodium channel blockers such as lidocaine, GSK-2339345, benzonatate and CNV1014802; dual N-methyl-D-aspartate (NMDA) receptor antagonist and sigma-1 agonist such as dextromethorphan; NMDA receptor antagonists such as memantine; opioids such as codeine and morphine; GABA analogues for example gabapentin and pregabalin; GABA-B receptor agonist such as baclofen; norepinephrine; serotonin/norepinephrine reuptake inhibitors such as amytripyline; Nociceptin/orphanin FQ (NOP)-1 agonists such as SCH486757; P2X3 purinergic receptor antagonists such as AF-219, AF-130 or substituted imidazopyridine compounds of formula (I) or a salt thereof

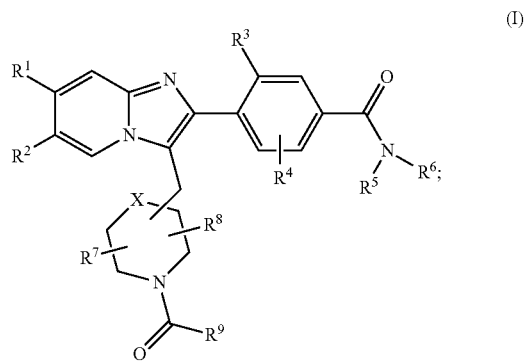

wherein:

R¹ is selected from the group consisting of cyano, halogen, methyl, and ethyl;

R² is selected from the group consisting of hydrogen, halogen, methyl, and ethyl;

R³ is selected from the group consisting of halogen, methyl, and ethyl;

R⁴ is selected from the group consisting of hydrogen, halogen, methyl, ethyl, and methoxy;

as to R⁵ and R⁶:

R⁵ and R⁶ are independently selected from the group consisting of hydrogen, $C_1$-$C_6$-alkyl, and hydroxy-$C_1$-$C_6$-alkyl; or R⁵ and R⁶, together with the nitrogen to which they are both attached, form a 5- or 6-member heterocycloalkyl, wherein:

the heterocycloalkyl is optionally substituted with one or more substituents independently selected from the group consisting of halogen, hydroxyl, and $C_1$-$C_4$-alkyl;

R⁷ and R⁸ are independently selected from the group consisting of hydrogen and $C_1$-$C_4$-alkyl;

R⁹ is selected from the group consisting of $C_1$-$C_6$-alkyl, $C_3$-$C_6$-cycloalkyl, $C_1$-$C_6$-alkyl-$C_3$-$C_6$-cycloalkyl, halo-$C_1$-$C_6$-alkyl, $C_1$-$C_6$-alkoxy, halo-$C_1$-$C_6$-alkoxy, and $C_1$-$C_6$-alkoxy-$C_1$-$C_6$-alkyl; and X is selected from a bond, CH₂, and O, including BLU-5937, (S)-methyl-2-((2-(2,6-difluoro-4-(methylcarbamoyl)phenyl)-7-methylimidazol[1.2-a]pyridin-3-yl)methyl)morpholine-4-carboxylate

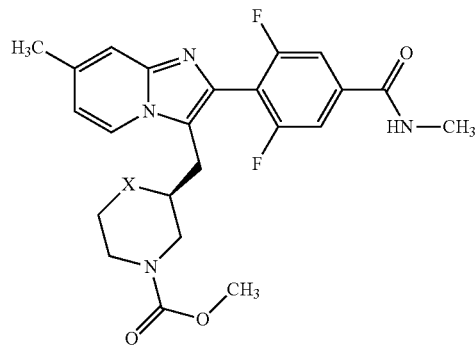

and (R)-methyl-2-((2-(2,6-difluoro-4-(methylcarbamoyl)phenyl)-7-methylimidazol[1.2-a]pyridin-3-yl)methyl)morpholine-4-carboxylate

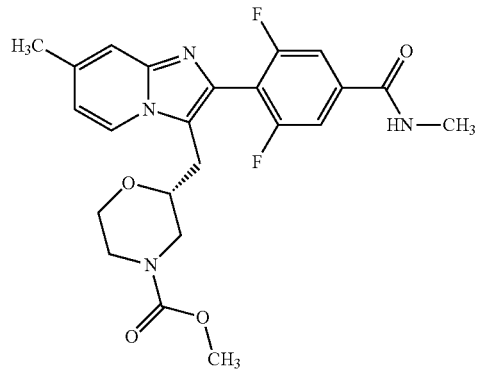

all described in U.S. Pat. No. 9,598,409 incorporated herein by reference in its entirety; Histamine-1 receptor antagonists such as chlorpheniramine, azelastine, mizolastine, loratadine and cetirizine; anticholinergic drugs such as caramiphen edisylate; secretolytic/mucolytic agents such as ambroxol, DWJ-1340 and HOB-048; Vanilloid-1 (TRPV-1) receptor antagonists such as PAC-14028, VR-611 and XEND-0501; Vanilloid-4 (TRPV-4) receptor antagonists such as GSK2193874 and GSK2798745; TRPM8 agonists such as menthol; homocysteine analogs such as erdosteine; corticosteroids such as budesonide and fluticasone; TRPA1 receptor antagonists such as HC-030031 and GRC-17536; 132-Agonists such as salbutamol; muscarinic receptor antagonists such as ipratropium bromide; proton pump inhibitors such as ranitidine and omeprazole; BK K+ channel inhibitors such as theophylline; mast cell stabilisers such as disodium cromoglycate; phosphodiesterase-(PDE)-4 inhibitors for example apremilast; cannabinoid receptor agonists such as CP55940 and JWH133; NK-1 and/or NK-2 or/and NK-3 antagonists or inhibitors of their cognate ligands NK-A and NK-B, inhibitors of SP for example anti-SP antibody; those of uncharacterised or unknown mechanism including levodropropizine, chlophedianol, carbetapentane (also known as pentoxyverine), levocloperastine, moguisteine, AG-1321001, CCP-01/05/06/07/08, AGPPC-709 and LPCN-1087.

In one embodiment, the present invention provides a combination which comprises (a) 2-(R)-(4-Fluoro-2-methyl-phenyl)-4-(S)-((8aS)-6-oxo-hexahydro-pyrrolo[1,2-α]-pyrazin-2-yl)-piperidine-1-carboxylic acid [1-(R)-(3,5-bis-trifluoromethyl-phenyl)-ethyl]-methylamide (orvepitant) or a pharmaceutically acceptable salt thereof and (b) a second drug substance and optionally one or more pharmaceutically acceptable excipient(s) for the treatment of chronic cough.

In one embodiment, the present invention provides a combination which comprises (a) 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) or a pharmaceutically acceptable salt thereof and (b) a second drug substance and optionally one or more pharmaceutically acceptable excipient(s) for the treatment of chronic refractory cough.

In a further embodiment, the present invention provides a combination of the compound(I)(orvepitant) or a pharmaceutically acceptable salt thereof with a second drug substance which is selected from is selected from a leukotriene receptor antagonist, voltage-gated sodium channel blockers, dual N-methyl-D-aspartate (NMDA) receptor antagonist and sigma-1 agonists, NMDA receptor antagonists, opioids, GABA analogues, GABA-B receptor agonist, serotonin/norepinephrine reuptake, Nociceptin/orphanin FQ (NOP)-1, P2X3 purinergic receptorantagonists, Histamine-1 receptor antagonists, anticholinergic drugs, secretolytic/mucolytic agents, Vanilloid-1 (TRPV-1) receptor antagonists, Vanilloid-4 (TRPV-4) receptor antagonists, homocysteine analogs, corticosteroids TRPA1 receptor antagonists, β2-Agonists; muscarinic receptor antagonists, proton pump inhibitors, BK K+ channel inhibitors, mast cell stabilisers, phosphodiesterase-(PDE)-4 inhibitors, cannabinoid receptor agonists, NK-1 and/or NK-2 or/and NK-3 antagonists or inhibitors of their cognate ligands NK-A and NK-B, inhibitors of SP and optionally one or more pharmaceutically acceptable excipient(s) for the treatment of chronic cough.

In a further embodiment, the present invention provides a combination of the compound(I) (orvepitant) or a pharmaceutically acceptable salt thereof with a second drug substance which is selected from is selected from a leukotriene receptor antagonist, voltage-gated sodium channel blockers, dual N-methyl-D-aspartate (NMDA) receptor antagonist and sigma-1 agonists, NMDA receptor antagonists, opioids, GABA analogues, GABA-B receptor agonist, serotonin/norepinephrine reuptake, Nociceptin/orphanin FQ (NOP)-1, P2X3 purinergic receptor antagonists, Histamine-1 receptor antagonists, anticholinergic drugs, secretolytic/mucolytic agents, Vanilloid-1 (TRPV-1) receptor antagonists, Vanilloid-4 (TRPV-4) receptor antagonists, homocysteine analogs, corticosteroids TRPA1 receptor antagonists, β2-Agonists; muscarinic receptor antagonists, proton pump inhibitors, BK K+ channel inhibitors, mast-cell stabilisers, phosphodiesterase-(PDE)-4 inhibitors; cannabinoid receptor agonists, NK-1 and/or NK-2 or/and NK-3 antagonists or inhibitors of their cognate ligands NK-A and NK-B, inhibitors of SP and optionally one or more pharmaceutically acceptable excipient(s) for the treatment of chronic refractory cough.

In a further embodiment, the present invention provides a combination of the compound(I) (orvepitant) or a pharmaceutically acceptable salt thereof with a second drug substance which is selected from P2X3 purinergic receptor antagonists such as AF-219, AF-130, substituted imidazopyridine compounds including BLU-5937, or mast cell stabilisers such as disodium cromoglycate or GABA analogues such as gabapentin or pregabalin or opioids such as codeine and morphine, and optionally one or more pharmaceutically acceptable excipient(s) for the treatment of chronic refractory cough or chronic refractory cough.

AF-219 corresponds to compound 5-(2,4-diamino-pyrimidin-5-yloxy)-4-isoproply-2-methoxy-benzenesulfonamide.

In one embodiment the maleate salt of orvepitant is utilized in a combination with a second drug substance as above described.

In a further embodiment, orvepitant maleate Form 1 is utilized in a combination with a second drug substance as above described.

It will be appreciated by those skilled in the art that the compound (I) or pharmaceutically acceptable salts thereof when used the treatment of ILDs. for may advantageously be used in combination with one or more other therapeutic agents for instance with: pirfenidone a broad-spectrum anti-inflammatory and anti-fibrotic of unknown mechanism; also deuterium-substituted pirfenidone; compounds such as inhibitors of the receptor kinase receptors, platelet-derived growth factor receptor (PDGFR), fibroblast growth factor receptor (FGFR) and vascular endothelial growth factor receptor (VEGFR) such as nintedanib: PBI-4050 an anti-fibrotic of unknown mechanism; lysophosphatidic acid (LPA)-1 antagonists such as AM095, AM152, AM966, Ki16425, SAR100842, BMS-986020 and UD-009; LPA-2 receptor agonists such as (R)-1-phenylethyl-5-(4-biphenyl-4-cyclopropanecarboxylic acid)-3-methylisoxazole-4-yl carbamate sodium salt; LPA-2 antagonists such as H2L5186303; Nadph oxidase (NOX)-4 inhibitors such as GLX351322 and 2-(2-chlorophenyl)-4-[3-(dimethylamino)phenyl]-5-methyl-1H-pyrazolo[4,3-C]pyridine-3,6(2H,5H)-dione; NOX-1,4 inhibitors such as GKT831; c-Jun amino-terminal kinase (JNK) inhibitors such as tanzisertib (CC-930) and CC-90001; compounds of unknown mechanism such as 3-pentylbenzenacetic acid sodium salt; type-A selective endothelin receptor antagonists such as ambrisentan; copper chelators such as tetrathiomolybdate; anti-IL-4 receptor antibodies (that therefore target IL-4 and IL-13) such as dupilumab; bispeciifc anti-IL-4/IL-13 antibodies such as SAR156597; dual endothelin receptor antagonists such as bosentan, macitentan, tezosentan, macitentan; anti-CC-chemokine ligand 2 (CCL2) antibodies such as carlumab (CNTO 888); anti-IL-13 antibodies such as QAX576I, lebrikizumab and tralokinumab; anti-L13 antibodies linked to a mutated form of pseudomonas exotoxin A such as cintredekin besudotox; anti-transforming growth factor-beta (TGFβ) antibodies such as fresolimumab (GC1008): anti-connective tissue growth factor monoclonal antibodies such as FG-3019; anti-αvβ6 integrin antibodies such as 264RAD and STX-100; integrin αvβ6 antagonists such as GSK 3008348: anti-lysyl oxidase-like 2 (LOXL2) antibodies such as simtuzumab; anti-chemokine (C—C motif) CCL-24 (also known as myeloid progenitor inhibitory factor 2 (MPIF-2) or eosinophil chemotactic protein 2 (eotaxin-2)) antibodies such as CM-101; purified bovine Type V Collagen oral solutions such as IW00; recombinant human pentraxin-2 (also known as serum amyloid P) such as PRM-151; NK-1 agonists such as [Sar9,Met(O2)11]-Substance P (NAS911B); a tetra-substituted porphyrin derivative containing manganese (III); antagonists of the leukotriene (LT) receptor combined with phosphodiesterases (PDE)-3,4; 5-lipoxygenase (5-LO) inhibitors such as tipelukast (MN-001); peroxisome proliferator-activated receptor pan-agonists such as 1-(6-Benzothiazolylsulfonyl)-5-chloro-1H-indole-2-butanoic acid; angiotensin II type-2 receptor (AT]-2 receptor agonists such as 3-[4-(1H-imidazol-1-ylmethyl)phenyl]-5-(2-methylpropyl)thiophene-2-[(N-butyloxylcarbamate)-sulphonamide] sodium salt and Compound 21; AT-2 receptor antagonists such as PD-123319; AT-1 receptor antagonists such as olmesartan medoxomil; PDE-5 inhibitors such as sildenafil, tadalafil and vardenafil; BCR-ABL tyrosine kinase inhibitors such as bafetinib (INNO-406), bosutinib (SKI-606), dasatinib (BMS-345825), imatinib, nilotinib (AMN107) and ponatinib (AP24534); synthetic prostacyclin analogues such as iloprost and cisaprost; anti-platelet agents such as treprostinil; lecithinized superoxide dismutase; beta-2 adrenoceptor agonists such as albuterol and salbutamol; mannose-6-phosphate derivatives such as PXS-25; galectin-3 inhibitors such as TD139; combinations of pentoxifylline and vitamin E such as PTL-202; MAPKAP Kinase 2 (MK2) inhibitors such as MMI-0100; hedgehog pathway inhibitors such as vismodegib; cysteine pro-drugs and glutathione precursors such as N-acetylcysteine; leukotriene A4 hydrolase (LTA4H) inhibitors such as acebilustat (CTX-4430); proton pump inhibitors such as omeprazole, lansoprazole, dexlansoprazole, rabeprazole, pantoprazole and esomeprazole; mast cell stabilisers (disodium cromoglycate) such as PA101; autotaxin inhibitors such as GLPG1690; recombinant human soluble thrombomodulin such as ART-123; P2X3 inhibitors such as AF-219 and AF-130 or substituted imidazopyridine compounds including BLU-5937; ROCK-2 inhibitors such as KD-025; anti-TNF antibodies such as etanercept, infliximab, adalimumab, certolizumab pegol and golimumab; PI3Kinase/mTOR inhibitors such as omipalisib (GSK2126458); hemoglobin modifiers such as GBT440; mesenchymal stem cell therapies such as Refacell-IPF; metalloporphyrins such as AEOL-10150; complement factor C3 inhibitors such as APL-1 and tryptophan hydroxylase 1 (TPH1) inhibitors such as KAR-5585.

In one embodiment, the present invention provides a combination which comprises (a) 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide(orvepitant)

or a pharmaceutically acceptable salt thereof and (b) a second drug substance and optionally one or more pharmaceutically acceptable excipient(s) for the treatment of ILDs.

In one embodiment, the present invention provides a combination which comprises (a) 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide(orvepitant) or a pharmaceutically acceptable salt thereof and (b) a second drug substance and optionally one or more pharmaceutically acceptable excipient(s) for the treatment of IPF.

In a further embodiment, the present invention provides a combination of the compound(I) (orvepitant) or a pharmaceutically acceptable salt thereof with a second drug substance which is selected from is selected from pirfenidone or nintedanib and optionally one or more pharmaceutically acceptable excipient(s) for the treatment of ILDs.

In a further embodiment, the present invention provides a combination of the compound(I) (orvepitant) or a pharmaceutically acceptable salt thereof with a second drug substance which is selected from is selected from pirfenidone or nintedanib and optionally one or more pharmaceutically acceptable excipient(s) for the treatment of IPF.

In one embodiment the maleate salt of orvepitant is utilized in a combination with a second drug substance as above described.

In a further embodiment, orvepitant maleate Form 1 is utilized in in a combination with a second drug substance as above described.

The following examples illustrate the invention without limiting the scope thereof.

Examples

Clinical Studies
Study Design for Chronic Refractory Cough

Orvepitant maleate Form 1 was evaluated in an open-label pilot study to determine the efficacy of multiple dosing in male and female patients with a diagnosis of chronic treatment-refractory cough for over 3 months. The study was a single-arm (30 mg orvepitant maleate Form 1 once daily), 4-week study with a 4 week follow-up. There were five scheduled clinic visits; Screening visit, Baseline visit, Week 1 visit, Week 4 visit (end of treatment period) and a Week 8 Follow-up visit.

The following instruments were used to assess efficacy:
Subjects were fitted with an ambulatory cough monitor (ACM) to record objective cough frequency over 24 hours at Screening, Weeks 1, 4 and 8
Cough-specific Quality of Life Questionnaire (CQLQ): Subjects were asked to complete this questionnaire at Screening, Weeks 1, 4 and 8
Global Rating of Change for Cough Frequency & Severity Scale: Subjects were asked to complete this scale at Weeks 1, 4 and 8
Cough Severity VAS: Subjects were issued with diaries for daily recording of Cough Severity VAS scores.

13 subjects were enrolled into the study and provided data on cough frequency, Cough QOL, Global Rating of Change for Cough Frequency and Severity, and Cough Severity VAS, but one of the 13 subjects had data missing on cough frequency (day and night) at week 4.

The primary endpoint was change in objective daytime cough frequency at the end of the treatment period at Week 4 compared to Baseline.

Results

Statistically significant improvements were seen in both objective and subjective measures of cough frequency and severity in this pilot study as well as in the Cough Quality of Life and Global Rate of Change assessments.

Primary Endpoint:

As illustrated in FIGS. 1 and 2 a significant reduction (−18.9 coughs/hr (−26%) mean change from Baseline), as derived from a negative binomial regression model, was observed for the primary endpoint of change in daytime objective cough frequency at Week 4 compared to Baseline (p<0.001).

Secondary Endpoints

Daytime Objective Cough Frequency: As provided in FIGS. 1 and 2 there was a significant reduction in daytime objective cough frequency at Week 1 (−27.0 coughs/hr (−38%) mean change from Baseline) and Week 8 (−20.4 coughs/hr (−28%) mean change from Baseline) (p=0.001 and p=0.02 respectively) but no significant change in daytime objective cough frequency at Week 8 compared to Week 4 (p=0.86).

Night-time Objective Cough Frequency: There was a significant reduction (−3.1 coughs/hr (−66%) mean change from Baseline) in night-time objective cough frequency at Week 8 compared to baseline (p=0.017), however there was no significant reduction in mean night-time objective cough frequency at Weeks 1 and 4 compared to Baseline, or between Weeks 4 and 8 (p=0.19, p=0.65, p=0.10 respectively).

Cough Quality of Life (CQLQ): The results of the CQLQ showed a significant reduction in the Overall score at Weeks 1, 4 and 8 compared to Baseline (mean changes of −4.0, −4.4 and −3.4; p<0.001, p=0.005 and p=0.033 respectively) and no significant difference in Overall score between Weeks 4 and 8 (p=0.52). Significant changes from Baseline were seen in most domains at either Week 1 or Week 4, with significant changes from Baseline seen at Weeks 1, 4 and 8 for both the Psychosocial and Extreme Physical domains. No significant changes were seen for the Emotional domain. There were no significant changes observed from Week 4 to Week 8 for any of the domains.

Global Rate of Change: More subjects felt better in terms of cough frequency at Week 1 (n=9) and Week 4 (n=7) compared to Baseline, than felt the same (n=4 and n=5 respectively). The median improvement score at both Weeks 1 and 4 was 3 (somewhat better). No subjects felt worse at Week 1 and Week 4. By Week 8, the number of subjects feeling better had reduced (n=3), with more feeling the same (n=7) and some feeling worse (n=3). Statistical significance was seen when using marginal homogeneity tests to compare the "better/same/worse" Week 8 results with Weeks 1 and 4 (p=0.02 and p=0.05 respectively), with fewer subjects feeling better at Week 8. More subjects felt better in terms of cough severity at Week 1 (n=8) compared to Baseline, than felt the same (n=5). The median improvement score was 4 (moderately better) at Week 1, and 3 (somewhat better) at Week 4. No subjects felt worse at either Week 1 or Week 4. By Week 8, the number of subjects feeling better had reduced (n=4), with more feeling the same (n=6) and some feeling worse (n=3). Statistical significance was seen when comparing the Week 8 results with Week 1 (p=0.05), with fewer subjects feeling better at Week 8. Adhoc analyses showed evidence of a relationship between objective and subjective ratings for changes in cough. Subjects who rated symptoms of cough frequency and cough severity as 'better', tended to have a greater decrease in daytime hourly cough rates than those who rated their symptoms as the same/worse. There was no apparent relationship with night-time hourly cough rates.

Cough Severity Visual Analogue Scale (VAS). A significant decrease from Baseline in daytime cough severity, as measured by the cough severity VAS, was observed by Week 2 of study (−39% average change from Baseline, p=0.002) and continued until Week 6 of study (−14% average change from Baseline, p=0.001). Likewise there was a significant decrease from Baseline in night-time cough severity by Week 1 of study (−14% average change from Baseline, p=0.01) which remained until Week 6 of study (−18% average change from Baseline, p=0.017).

Clinical Studies in Patients with IPF Associated Chronic Cough

Orvepitant maleate Form 1 is evaluated in a randomised, double-blind, placebo controlled study in patients with IPF associated chronic cough; breathlessness us assessed.

The study is a two-arm trial with 30 mg orvepitant maleate Form 1 and placebo administered once daily for 2-weeks with a 2-week follow-up. There are 25 subjects in each arm. There are 4 scheduled clinic visits; Screening visit, Baseline visit, Week 2 visit (end of treatment period) and a Week 4 Follow-up visit.

The following instruments are used to assess efficacy:
Subjects are fitted with an ambulatory cough monitor (ACM) to record objective cough frequency over 24 hours at Screening (Baseline value) and Week 2
Cough-specific Quality of Life Questionnaire: Subjects are asked to complete this questionnaire at Screening, Baseline, Weeks 2 and 4
Global Rating of Change for Cough Frequency & Severity Scale: Subjects are asked to complete this scale at Weeks 2 and 4
Cough Severity VAS: Subjects are issued with diaries for daily recording of Cough Severity VAS scores
Breathlessness scales. University of San Diego Shortness of Breath Questionnaire and Borg CR10 Scale. Subjects are asked to complete this questionnaire at Screening, Baseline, Weeks 2 and 4.

The primary endpoint is change in objective daytime cough frequency at the end of the treatment period at Week 2 compared to Baseline.

Clinical Studies in Patients with Chronic Cough Due to Lung Tumours

Orvepitant maleate Form 1 is evaluated in a randomised, double-blind, placebo controlled study in patients with patients with chronic cough due to lung tumours.

The study is a two-arm trial with 30 mg orvepitant maleate Form 1 and placebo administered once daily for 2-weeks with a 2-week follow-up. There are 25 subjects in each arm. There are 4 scheduled clinic visits; Screening visit, Baseline visit, Week 2 visit (end of treatment period) and a Week 4 Follow-up visit.

The following instruments are used to assess efficacy:
Subjects are fitted with an ambulatory cough monitor (ACM) to record objective cough frequency over 24 hours at Screening (Baseline value) and Week 2
Manchester Cough in Lung Cancer Scale Score (MCLCS)—quality of life score for lung cancer patients: Subjects are asked to complete this questionnaire at Screening, Baseline, Weeks 2 and 4
Global Rating of Change for Cough Frequency & Severity Scale: Subjects are asked to complete this scale at Weeks 2 and 4
Cough Severity VAS: Subjects are issued with diaries for daily recording of Cough Severity VAS scores
Breathlessness scales. University of San Diego Shortness of Breath Questionnaire or/and Borg CR10 Scale or/and Cancer Dyspnea Scale. Subjects are asked to complete this questionnaire at Screening, Baseline, Weeks 2 and 4.

The primary endpoint is change in objective daytime cough frequency at the end of the treatment period at Week 2 compared to Baseline.

IDLs Therapeutic Indication

In Vitro Assays

The use of compound of formula(I) or pharmaceutically acceptable salts thereof as an anti-IPF agent can be assessed in one or more of the in-vitro assays as described below. Appropriate human cell lines together with human primary lung cells from normal and IPF donors may be utilised in these assays.

Lung Epithelial Cell Activation Assays

The effect of the compound of formula(I) or pharmaceutically acceptable salts thereof to inhibit the activation by Substance P of lung epithelial cells that respond by releasing 'alarmins' and growth factors such as TGF-$\beta$is is assayed. These alarmins that include Heat Shock Protein 60 (HSP-60), high-mobility group box-1 protein (HMGB1) and interleukin (IL)-1$\alpha$, are inflammatory molecular 'danger signals' released by injured epithelial cells that can contribute to the innate immune response by activating immune cells and other cell types to release fibroblast activating mediators that may include growth factors. The alarmins and growth factors released by epithelial cells can also have a direct stimulatory effect upon fibroblasts. The stimulated fibroblasts respond by migrating and proliferating as well as differentiating to myofibroblasts, and by overexpressing fibrotic matrix proteins and inducing further expression of profibrotic cytokines and growth factors such as connective tissue growth factor (CTGF), resulting in extracellular matrix deposition and progressive fibrosis.

The human epithelial cell lines used include BEAS-2B, H358, HPL1D, VA10, 16HBE14o and A549, or human primary lung normal epithelial cells or human primary lung epithelial cells from IPF donors. The enhanced amount of alarmins and growth factors produced by Substance P induced activation of human epithelial cells, and their inhibition by co-administration of compound of formula(I) or pharmaceutically acceptable salts thereof are measured using for instance mRNA profiling or enzyme-linked immunosorbent assay (ELISA) methods.

Inflammatory Responses by Immune Cells Such as Macrophages

The effect of the compound of formula(I) or pharmaceutically acceptable salts thereof to inhibit the activation by Substance P of human lung macrophages that respond by releasing inflammatory and profibrotic mediators is assayed.

Human macrophage cell lines used include U937cells, human primary normal lung macrophage cells or human primary lung macrophage cells from IPF donors. The enhanced amount of inflammatory mediators such as CCL-17, CCL-18, CCL-22, IL-6, IL-10 and the growth factor TGF-$\beta$, produced by Substance P activated human lung macrophage cells, and their inhibition by co-administration of compound of formula(I) or pharmaceutically acceptable salts thereof, are measured using for instance mRNA profiling or ELISA assay methods.

Inflammatory Responses by Immune Cells such as Mast Cells

The effect of the compound of formula(I) or pharmaceutically acceptable salts thereof to inhibit the activation by Substance P of human lung mast cells that respond by releasing an array of profibrotic mediators such as tryptase, chymase, TGF-β, IL-13, CCL2, CCL5, IL-4, PDGF and FGF, are assayed.

Human mast cell lines used include HMC-1, LAD2, and LUVA cells, human primary lung normal mast cells or human primary lung mast cells from IPF donors. The enhanced amount of any one or more of the profibroitc mediators tryptase, chymase, TGF-β, IL-13, CCL2, CCL5, IL-4, PDGF and FGF produced by Substance P activated human lung mast cells, and their inhibition by co-administration compound of formula(I) or pharmaceutically acceptable salts thereof, are measured using for instance mRNA profiling or ELISA assay methods.

Inflammatory Responses by Immune Cells Such as T-Cells

The effect of the compound of formula(I) or pharmaceutically acceptable salts thereof to inhibit T cell activation, polarisation and survival, that is necessary for innate and adaptive cellular immune responses in IPF, and are promoted by Substance P are assayed.

Human T-cell lines can be used or human primary lung isolated T cells or human primary lung isolated T-cells from IPF donors. The enhanced amount of any one or more of the effector molecules IFN-g, IFN-γ, IL-2, IL-4, IL-5, IL-8, IL-10, IL-12p70, IL-13, IL-17, IL-23 and TNF-a produced by Substance P activated human T cells, and their inhibition by co-administration compound of formula(I) or pharmaceutically acceptable salts thereof, are measured using for instance mRNA profiling or ELISA assay methods.

Lung Fibroblast Activation, Migration and Differentiation

The effect of the compound of formula(I) or pharmaceutically acceptable salts thereof to inhibit the activation by Substance P of human lung fibroblast proliferation, migration and differentiation to myofibroblasts is assayed.

Human lung fibroblast cell lines used include WI38, MRCS, HFL1, HDF and IMR90, or human primary lung normal fibroblasts or human primary lung fibroblasts from IPF donors.

Human lung fibroblast proliferation induced by Substance P and its inhibition by co-administration of compound of formula(I) or pharmaceutically acceptable salts thereof can be assayed by a number of techniques including measuring the amount of either thymidine or 5-bromo-2'-deoxyuridine (BrdU) incorporated into replicating DNA of proliferative fibroblasts. Alternatively, the metabolic activity of human lung fibroblasts may be used as a measure of cell proliferation. These assays involve the use of tetrazolium salts or Alamar Blue compounds that become reduced in the environment of metabolically active cells, forming a formazan dye that subsequently changes the colour of the media, which is measured spectrophotometrically.

Human lung fibroblast migration is assayed in a Boyden chamber system. The upper and lower portions of the chamber are separated by a pore filter; with the human lung fibroblasts placed in the upper chamber while a chemotractant such as fibronectin is placed in the lower chamber. Migration is assessed following incubation by counting the number of cells on the filter using a light microscope or cell counter. The ability of the compound of formula(I) or pharmaceutically acceptable salts thereof to inhibit Substance P promoted chemotaxis by human lung fibroblasts is determined.

The differentiation of human lung fibroblasts to myofibroblasts is assayed by incubation of human lung fibroblasts with TGF-β or/and Substance P or co-administration of TGF-β and Substance P, and assaying for the expression of the myofibroblast marker alpha-smooth muscle actin (α-SMA) by using mRNA profiling or ELISA or fluorescent imaging methods for instance. The ability of the compound of formula(I) or pharmaceutically acceptable salts thereof to inhibit TGF-β or/and Substance P or co-administered TGF-β and Substance P promoted human lung fibroblast transition to myofibroblasts is determined.

Lung Fibroblast and Myofibroblast Extracellular Matrix Deposition

The effect of the compound of formula(I) or pharmaceutically acceptable salts thereof to inhibit the Substance P induced deposition of extracellular matrix (ECM) is assayed.

Human lung fibroblast cell lines used include MRCS, or human primary lung normal myofibroblasts or human primary lung myofibroblasts from IPF donors is used. The protein or/and mRNA expression by human lung fibroblasts or/and human lung myofibroblasts of one or more constituents of ECM such as the fibrous proteins collagen, elastin, fibronectin or laminin, that are induced by Substance P and inhibited by co-administration of the compound of formula (I) or pharmaceutically acceptable salts thereof, is measured by a range of mRNA profiling or ELISA assay techniques respectively.

Angiogenesis

The effect of the compound of formula(I) or pharmaceutically acceptable salts thereof in inhibiting angiogenesis by endothelial cells that is promoted by Substance P is assayed.

Human lung endothelial cells lines used include PCS-100-022, or human primary lung normal endothelial cells or human primary lung endothelial cells from IPF donors are used Angiogenesis of cultured human lung endothelial cells stimulated by Substance P and inhibited by co-administration of the compound of formula(I) or pharmaceutically acceptable salts thereof, may be evaluated by using a matrigel endothelial cell tube formation assay.

Co-Culture Combinations

Co-culture of two or more different combinations of human lung: epithelial cells, fibroblasts, myofibroblasts, macrophages, mast and endothelial cells are used. Such as human lung epithelial cells with human lung fibroblasts; or human lung mast cells with human lung fibroblasts; or human lung macrophages with human lung fibroblasts; etc. Combinations of two or more of these human lung cells are built into 3-dimensional models using scaffolds. The effect of Substance P on such co-cultured systems are explored using the assay formats described above such as lung epithelial cell activation, inflammatory responses by immune cells such as macrophages and mast cells, fibroblast proliferation, migration and differentiation to myofibroblasts, ECM deposition and promotion of angiogenesis. The ability of the compound of formula(I) or pharmaceutically acceptable salts thereof, to inhibit these Substance P promoted deleterious activities may be determined.

Clinical Study

The efficacy of compound of formula(I) or pharmaceutically acceptable salts thereof as a monotherapy or as an add-on to a standard-of-care IPF treatment that patients are stably administered for at least 3 months such as pifenidone or nintedanib, are evaluated in a 52-week, placebo controlled, double-blind, randomised study in patients who have a diagnosis of IPF and who have a forced vital capacity (FVC) percent of predicted value 50% and 100% at screening.

The primary endpoint for efficacy is assessed as the change from Baseline to Week 52 in the annual rate of decline in percent predicted FVC. Secondary endpoints include change from baseline to Week 52 in:

Progression Free Survival (PFS)

pulmonary fibrosis score by high-resolution chest computed tomography;

pulmonary function as measured by FVC annualized rate of change in FVC diffusion capacity of the lung for carbon monoxide health-related quality of life scores six-minute walk test time from randomization to first event of an acute IPF exacerbation Pharmaceutical Compositions Orvepitant maleate Form 1 will normally, but not necessarily, be formulated into pharmaceutical compositions prior to administration to a patient. In one aspect, the invention is directed to pharmaceutical compositions comprising orvepitant maleate Form 1.

Tablets of orvepitant maleate Form 1 have been formulated as white to off-white, film-coated round tablets containing 10 mg, 20 mg, 30 mg, 50 mg and 60 mg of orvepitant which provide an immediate release of the active ingredient for oral administration.

The list of excipients and quantitative composition of tablets are reported in Tables 1-3

TABLE 1

Composition of Tablets Orvepitant Maleate Form 1

| Component | Quantity (mg/tablet) | | | | Function |
| --- | --- | --- | --- | --- | --- |
| | 10 mg | 30 mg | 50 mg | 60 mg | |
| Tablet core | | | | | |
| Orvepitant maleate Form 1 | 11.85[1] | 35.54[2] | 59.23[3] | 71.09[4] | Active |
| Microcrystalline cellulose | 60.00 | 149.22 | 60.00 | 79.39 | Filler |
| Lactose monohydrate | 201.90 | 95.54 | 154.52 | 122.12 | Filler |
| Croscarmellose sodium | 9.00 | 5.92 | 9.00 | 11.85 | Disintegrant |
| Hypromellose | 15.00 | 10.78 | 15.00 | 12.55 | Binder |
| Magnesium stearate | 2.25 | 3.00 | 2.25 | 3.00 | Lubricant |
| Purified water[5] | qs | qs | qs | qs | Granulating fluid |
| Total unit dose | 300.00 | 300.00 | 300.00 | 300.00 | — |
| Coat | | | | | |
| Opadry ® White OY-S-28876 | 9.00 | 9.0 | 9.00 | 9.0 | Coating agent |
| Purified water[5] | qs | qs | qs | qs | Suspending agent |

Note:
[1]Corresponding to 10.0 mg as orvepitant
[2]Corresponding to 30.0 mg as orvepitant
[3]Corresponding to 50.0 mg as orvepitant
[4]Corresponding to 60.0 mg as orvepitant
[5]Removed during processing. Does not appear in the final product.

TABLE 2

Orvepitant maleate Form 1 30% w/w granulate

| Material and Specification | Master Unit Formula Quantity (% w/w) |
| --- | --- |
| Orvepitant maleate | 30.00* |
| Hypromellose 2910 | 5.00 |
| Lactose monohydrate | 33.50 |
| Microcrystalline cellulose | 30.00 |
| Croscarmellose Sodium | 1.50 |

*corresponding to 25.32% w/w as free base

TABLE 3

Composition of Orvepitant Maleate Form 1 Tablets

| Component | Quantity (mg/tablet) | | | Function |
| --- | --- | --- | --- | --- |
| | 10 mg | 20 mg | 30 mg | |
| Tablet core | | | | |
| Orvepitant maleate[1] granule of Table 2 (30.00% w/w) | 39.49[2] | 78.99[3] | 118.48[4] | Active |
| Lactose monohydrate | 188.51 | 149.01 | 109.52 | Filler |
| Microcrystalline cellulose | 60.00 | 60.00 | 60.00 | Filler |
| Croscarmellose sodium | 9.00 | 9.00 | 9.00 | Disintegrant |
| Magnesium stearate[5] | 3.00 | 3.00 | 3.00 | Lubricant |

TABLE 3-continued

Composition of Orvepitant Maleate Form 1 Tablets

| Component | Quantity (mg/tablet) | | | Function |
|---|---|---|---|---|
| | 10 mg | 20 mg | 30 mg | |
| Purified water[6] | qs | qs | qs | Granulating fluid |
| Total unit dose | 300.00 | 300.00 | 300.00 | — |
| Coat | | | | |
| Opadry ® White OY-S-28876[7] | 9.0[7] | 9.0[7] | 9.0[7] | Coating agent |
| Purified water[6] | qs | qs | qs | Suspending agent |

[1]The actual quantity of orvepitant maleate Form 1 may be adjusted based on the purity of the imput drug substance.
[2]Corresponding to 10.0 mg as orvepitant
[3]Corresponding to 20.0 mg as orvepitant
[4]Corresponding to 30.0 mg as orvepitant
[5]Vegetable origin.
[6]Removed during processing. Does not appear in the final product.
[7]The weight of film coat applied per tablet may vary depending on the efficiency of the process, but is typically 3% w/w of tablet core weight.

Orvepitant maleate tablets, 10 mg, 20 mg, 30 mg, 50 mg, and 60 mg were manufactured using wet granulation, dry blending, tablet compression and film coating processes.

Orvepitant maleate as drug substance, lactose monohydrate, hypromellose, microcrystalline cellulose and croscarmellose sodium were sieved and dry mixed into the high shear mixer granulator for approximately 5 minutes. The granulation water was sprayed onto the drug substance, lactose monohydrate, hypromellose, microcrystalline cellulose and croscarmellose sodium dry blend. The wet granule was dried approximately at 65° C. into a fluid bed dryer for approximately 45 minutes (<2% LOD), milled using a conical mill (screen size 813 µm) and blended into a bin blender with lactose monohydrate, microcrystalline cellulose and croscarmellose sodium for approximately 20 minutes. Magnesium stearate was added for lubrication into the bin blender and the mixture was blended for approximately 3 minutes.

The blend was compressed using a suitable rotary tablet compression machine to obtain uncoated tablets. Opadry® White OY-S-28876 was charged into a mixing vessel with purified water and the film coating suspension prepared with stirring. The tablets were film coated into a suitable pan coater (approximately 3% weight gain).

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way.

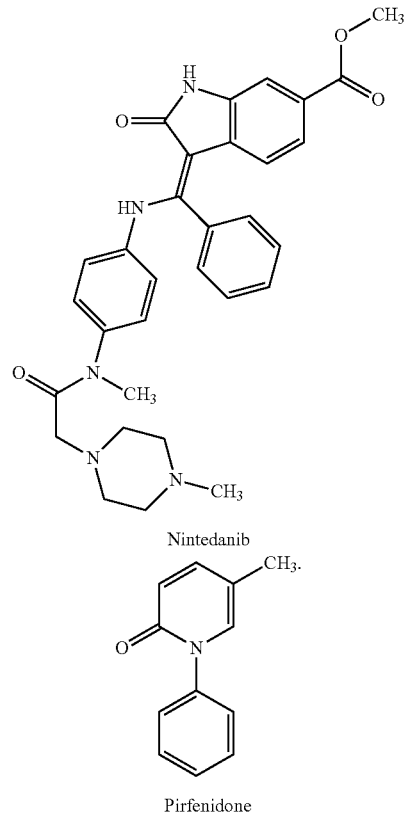

Nintedanib

Pirfenidone

The invention claimed is:

1. A method of treatment of chronic cough, comprising administering to a human in need thereof a therapeutically effective amount of compound 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (orvepitant) or a pharmaceutically acceptable salt thereof in combination with one or more therapeutic agents selected from a P2X3 purinergic receptor antagonist, nintedanib, pirfenidone and deuterium-substituted pirfenidone:

2. A method of treatment according to claim 1, wherein the chronic cough is chronic refractory cough.

3. A method of treatment according to claim 1, wherein the chronic cough is due or associated with sarcoidosis, emphysema or idiopathic pulmonary fibrosis.

4. A method of treatment according to claim 1, wherein the chronic cough is due or associated with asthma, chronic bronchitis, chronic postnasal drip, eosinophilic bronchitis and chronic obstructive pulmonary disease.

5. A method of treatment according to claim 1, wherein the chronic cough is due or associated with chronic infections such as bronchiectasis, tuberculosis, cystic fibrosis.

6. A method of treatment according to claim 1, wherein the chronic cough is due or associated with tumours such as bronchogenic carcinoma, alveolar cell carcinoma, benign airway tumours, mediastinal tumours.

7. A method of treatment according to claim 1, wherein the chronic cough is due or associated with a cardiovascular disease such as left ventricular failure, pulmonary infarction, aortic aneurysm.

8. A method of treatment according to claim 1, wherein the chronic cough is due or associated with reflux oesophagitis, recurrent aspiration, endobronchial sutures, postnasal drip syndrome or rhinosinusitis.

9. A method of treatment according to claim 1, wherein the pharmaceutically acceptable salt of the compound is maleate.

10. A method of treatment according to claim 1, wherein the compound is orvepitant maleate Form 1.

11. A method of treatment according to claim 1, wherein the P2X3 purinergic receptor antagonist are the compounds 5-(2,4-diamino-pyrimidin-5-yloxy)-4-isoproply-2-methoxy-benzenesulfonamide (AF-219), AF-130 or substituted imidazopyridine compounds, wherein said imidazopyridine compounds are compounds of formula (I) or a salt thereof

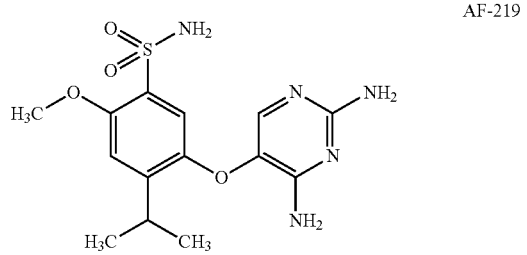
AF-219

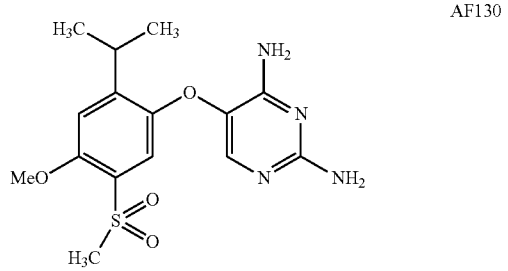
AF130

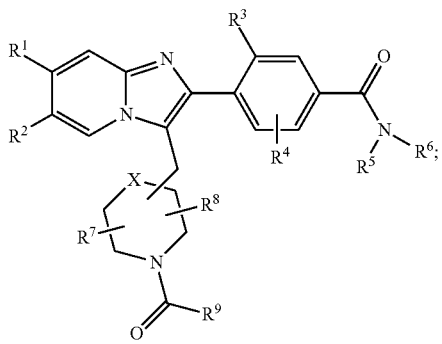
(I)

wherein:
R1 is selected from the group consisting of cyano, halogen, methyl, and ethyl;
R2 is selected from the group consisting of hydrogen, halogen, methyl, and ethyl;
R3 is selected from the group consisting of halogen, methyl, and ethyl;
R4 is selected from the group consisting of hydrogen, halogen, methyl, ethyl, and methoxy;
as to R5 and R6:
R5 and R6 are independently selected from the group consisting of hydrogen, C1-C6-alkyl, and hydroxy-C1-C6-alkyl; or
R5 and R6, together with the nitrogen to which they are both attached, form a 5- or 6-member heterocycloalkyl, wherein:
the heterocycloalkyl is optionally substituted with one or more substituents independently selected from the group consisting of halogen, hydroxyl, and C1-C4-alkyl;
R7 and R8 are independently selected from the group consisting of hydrogen and C1-C4-alkyl;
R9 is selected from the group consisting of C1-C6-alkyl, C3-C6-cycloalkyl, C1-C6-alkyl-C3-C6-cycloalkyl, halo-C1-C6-alkyl, C1-C6-alkoxy, halo-C1-C6-alkoxy, and C1-C6-alkoxy-C1-C6-alkyl; and
X is selected from a bond, CH2, and O.

12. A method of treatment according to claim 1, wherein the P2X3 purinergic receptor antagonist is the compound 5-(2,4-diamino-pyrimidin-5-yloxy)-4-isoproply-2-methoxy-benzenesulfonamide (AF-219) or AF-130.

13. A method of treatment according to claim 1, wherein the therapeutic agent is pirfenidone or deuterium-substituted pirfenidone.

14. A method of treatment according to claim 1, wherein the therapeutic agent is pirfenidone.

15. A method of treatment according to claim 1, wherein the therapeutic agent is nintedanib.

* * * * *